United States Patent [19]

Leckrone et al.

[11] Patent Number: 4,485,818
[45] Date of Patent: Dec. 4, 1984

[54] MULTI-MODE MICROPROCESSOR-BASED PROGRAMMABLE CARDIAC PACER

[75] Inventors: Michael E. Leckrone, Fort Lauderdale; Vincent T. Cutolo, Jr., Miami, both of Fla.

[73] Assignee: Cordis Corporation, Miami, Fla.

[21] Appl. No.: 207,003

[22] Filed: Nov. 14, 1980

[51] Int. Cl.³ .............................................. A61N 1/36
[52] U.S. Cl. .............................................. 128/419 PG
[58] Field of Search .................... 128/419 PG, 419 PT

[56] References Cited

U.S. PATENT DOCUMENTS

| | | | |
|---|---|---|---|
| 4,038,991 | 8/1977 | Walters | 128/419 PG |
| 4,114,627 | 9/1978 | Lewyn et al. | 128/419 PG |
| 4,166,470 | 9/1979 | Neumann | 128/419 PG |
| 4,181,133 | 1/1980 | Kolenik et al. | 128/419 PG |
| 4,222,385 | 9/1980 | Backhouse | 128/419 PG |
| 4,312,355 | 1/1982 | Funke | 128/419 PG |
| 4,313,441 | 2/1982 | Buffet | 128/419 PG |

FOREIGN PATENT DOCUMENTS

| | | | |
|---|---|---|---|
| 2738871 | 3/1978 | Fed. Rep. of Germany | 128/419 PG |
| 2026870 | 2/1980 | United Kingdom | 128/419 PG |

Primary Examiner—William E. Kamm
Attorney, Agent, or Firm—Kenway & Jenney

[57] ABSTRACT

An implantable, microprocessor-based cardiac pacer provides physiologically adaptive pacing in four fundamental modes: ventricular-inhibited; atrial-synchronized ventricular with or without ventricular sensing; and atrial-ventricular (AV) sequential. In the AV sequential mode, the pacer automatically shifts to atrial synchronous ventricular pacing when the atrial rate exceeds the programmed minimum rate. Temporary pacing modes are available for treatment of arrhythmia and either atrial or ventricular overdrive pacing via chest wall stimulation. The pacer continuously monitors tachyarrhythmia and automatically enters and exits a special arrhythmia response mode. Eight parameters can be altered one at a time or reprogrammed to a standard set in a single programming step using pre-existing magnetic programmers. A weak battery is signified by substituting a lower frequency voltage-sensitive backup oscillator and by dropping the atrial beat in the magnet rate. Sense amplifier blanking is executed in software while rate limit is executed in both software and separate hardware circuits.

8 Claims, 28 Drawing Figures

```
!M
0000  F810 E866 6FF8 01BB F8B6 AAF8 BAAE F800;
0010  B6A6 BABC BDBE BFB9 A9B7 A7F8 D5AC F8D1;
0020  ADF8 D9AE F8DC AFF8 01B1 F8B4 A1E0 7020;
0030  F800 A8F8 16A4 1889 3A5B 993A 6235 64EF;
0040  88F5 3279 EC88 F533 8798 3AB4 3427 ED88;
0050  F53A AAE3 6163 9AB2 8AA2 D229 C4C4 1222;
0060  3044 303F EF88 F533 76F0 A8F8 16A9 8632;
0070  8526 1222 3083 1230 6BE3 6963 9BB2 8BA2;
0080  D2C4 C430 AA30 8198 3A85 843A 9134 9630;
0090  9424 349F 30AA 1616 86FF 0633 B130 2716;
00A0  1686 FF06 33B1 C4C4 3036 C4C4 C4C4 1230;
00B0  36C0 0349 304E 6BF8 49A0 F816 A4F8 01A8;
00C0  EA99 3ACD 3DCA F816 A9D0 1330 C930 CA55;
00D0  463C 352A 201A 174D 4138 3206 090C 127B;
00E0  7A13 30ED 7B7B 7A30 ED7B 7B7B 7AF8 00B0;
00F0  F836 A0F8 04A8 F821 A323 833A F9F8 12A4;
0100  236B D0F8 00A8 18EC 88F5 3330 341A F605;
0110  A323 833A 11ED 88F5 3A32 E363 7B7B 7B7B;
0120  7AF8 22A3 2383 3A24 F804 A8C4 C46B 3006;
0130  300E 1230 06E3 F800 A863 183E 56C4 C4C4;
0140  C4EF 88F5 3277 C4C4 C4C4 D1ED 88F5 325A;
0150  C4C4 1222 303A 6BC0 0216 3770 F801 A812;
0160  E361 7B7B 7B7B 7AF8 07A3 2383 3A6A 303A;
0170  F800 A822 1230 3A18 E369 1222 3062 7B7A;
0180  1323 3095 7B7B 7A13 3095 7B7B 7B7A 3095;
0190  7B7B 7B7B 7AF8 00B0 F836 A088 FC04 A8F8;
01A0  12A9 F81F A323 833A A586 32B1 2623 136B;
01B0  D023 30AE 7A17 3EC6 3EC6 3EC6 3EC6 3EC6;
01C0  3EC6 3EC6 3035 36B5 36B5 36B5 36B5 36B5;
01D0  36B5 36B5 87FF 08CB 0216 A7FA 60C2 022A;
01E0  FF20 CA02 1087 FA07 32F5 FF01 CA02 10E3;
01F0  6C65 6930 F9E3 6C65 61F8 02B0 F800 A0D0;
0200  F801 E1F8 B4A1 F800 A7A8 E070 20C0 0103;
0210  F800 B0F8 00A0 F802 B2F8 1DA2 D2F8 01B1;
0220  F8B4 A1F8 00A7 A8E2 7020 87FA 07CA 0255;
0230  87FA 18CA 023C B8E3 6465 30E5 FF08 3A46;
0240  B9E3 646D 30E5 FF08 3A50 B8E3 6C65 30E5;
0250  F810 B830 E5FF 013A 7D87 FA18 3A64 B9E3;
0260  6667 30E5 FF08 3A6E B9E3 666F 30E5 FF08;
0270  3A78 B9E3 6E67 30E5 F810 B930 E5FF 013A;
0280  A287 FA18 3293 FF08 3298 FF08 329D F8E9;
0290  AA30 E5F8 B6AA 30E5 F8DF AA30 E5F8 E4AA;
02A0  30E5 FF01 3AC7 87FA 1832 B8FF 0832 BDFF;
02B0  0832 C2F8 90AB 30E5 F87E AB30 E5F8 84AB;
02C0  30E5 F8BA AB30 E5FF 013A E8F8 D3AC 87FA;
02D0  1832 E5FF 0832 E0FF 0832 E31C 1C1C 30E5;
02E0  1C30 E51C 1CC0 0216 FF01 CA03 0BF8 CFAD;
02F0  87FA 1832 E5FF 08C2 0304 FF08 C203 071D;
0300  1D1D 3046 1D30 461D 1D30 46FF 013A 2CF8;
0310  D7AE 87FA 1832 46FF 08C2 0325 FF08 3228;
0320  1E1E 1E30 461E 1E30 461E 1E30 46F8 DBAF87;
0330  FA18 3246 FF08 3241 FF08 3244 1F1F 1F30;
0340  461F 3046 1F1F C002 16EC F0FC 04B5 A5F8;
0350  FFA4 F806 B6A6 A825 1896 32B5 8432 B924;
0360  3466 C4C4 306B EC88 F533 CE30 CA89 3AD3;
0370  35D7 853A E5E3 6369 F803 B28B A2D2 7B7A;
0380  1323 3095 7B7B 7A13 3095 7B7B 7B7A 3095;
0390  7B7B 7B7B 7A86 32F4 26F8 03B0 F857 A0F8;
03A0  04A8 95FF 04A5 F812 A9E3 F81E A323 833A;
03B0  AD13 236B D012 2230 60E3 95FC 01B5 EEF5;
03C0  32C7 F8FF A430 6DE6 30C5 1323 306D F802;
03D0  A630 CC29 E330 E5F8 16A9 F800 A895 A586;
03E0  32EC 2630 57C4 C4E3 C4C4 3057 0FA8 F800;
03F0  A4C0 0036 F800 B0A4 6BF8 36A0 0FA8 D0D4
```

FIG. 9

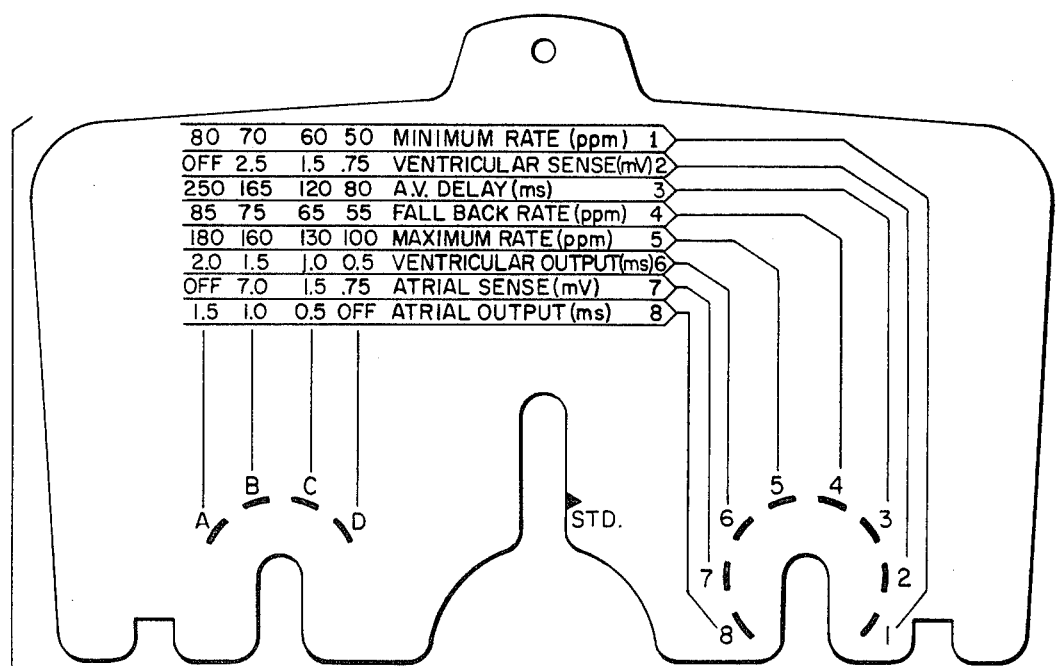
FIG. 14
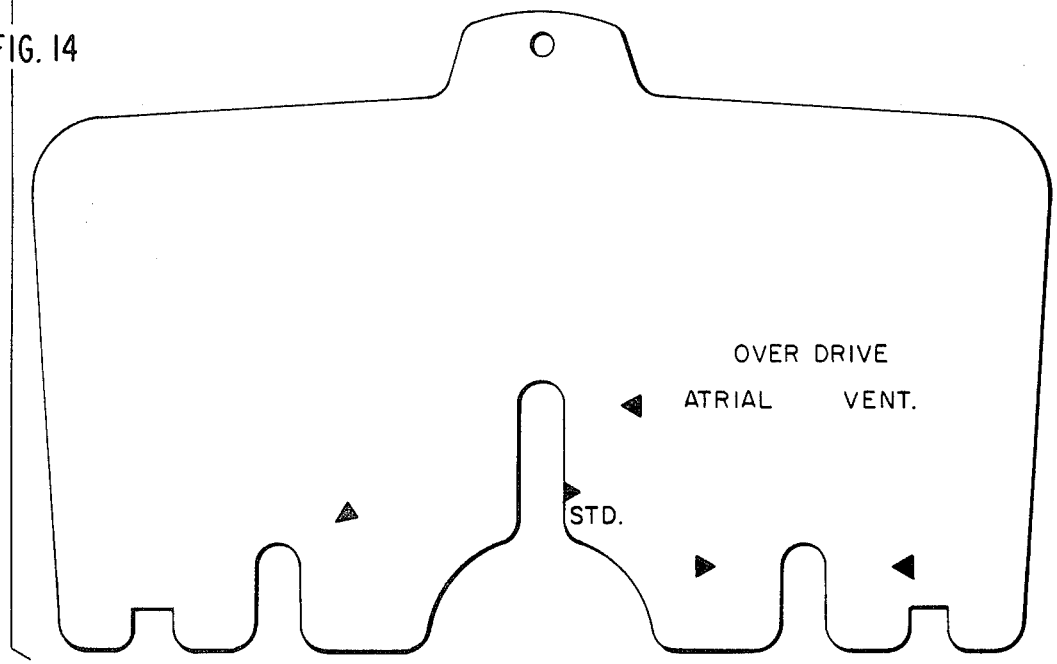
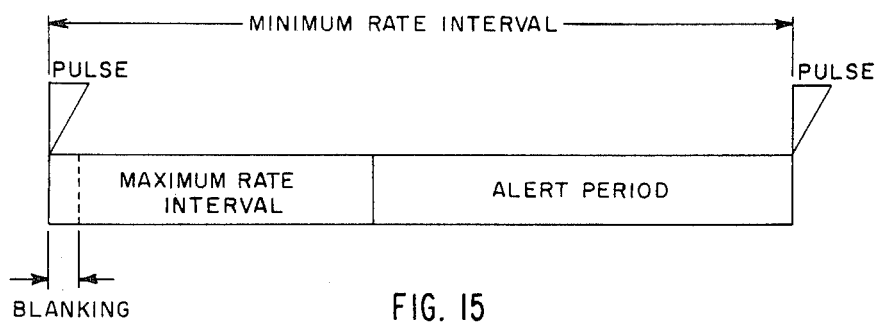
FIG. 15

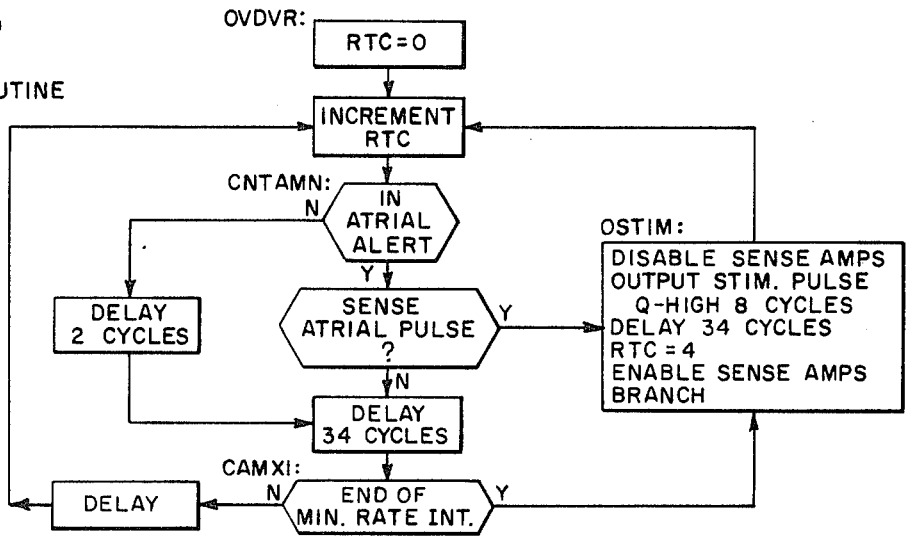
FIG. 16
OVERDRIVE ROUTINE
—NOTE—
ENTERS OVERDRIVE WITH PROPER STIMULUS CHANNEL ENABLED
EXIT OVERDRIVE ROUTINE ONLY BY PROGRAMMING INTERRUPT
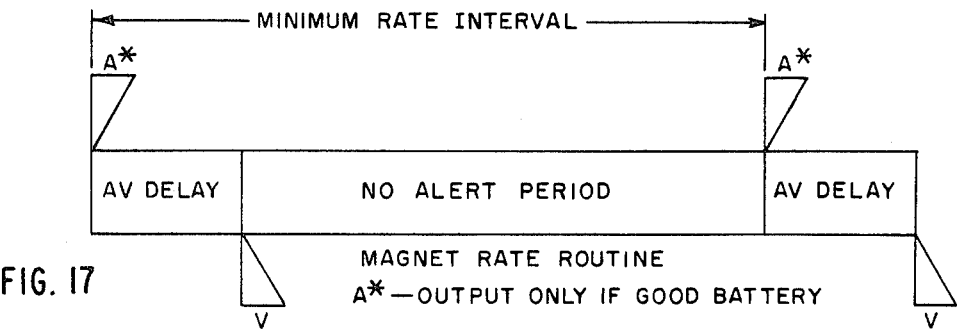
FIG. 17   MAGNET RATE ROUTINE
A*—OUTPUT ONLY IF GOOD BATTERY
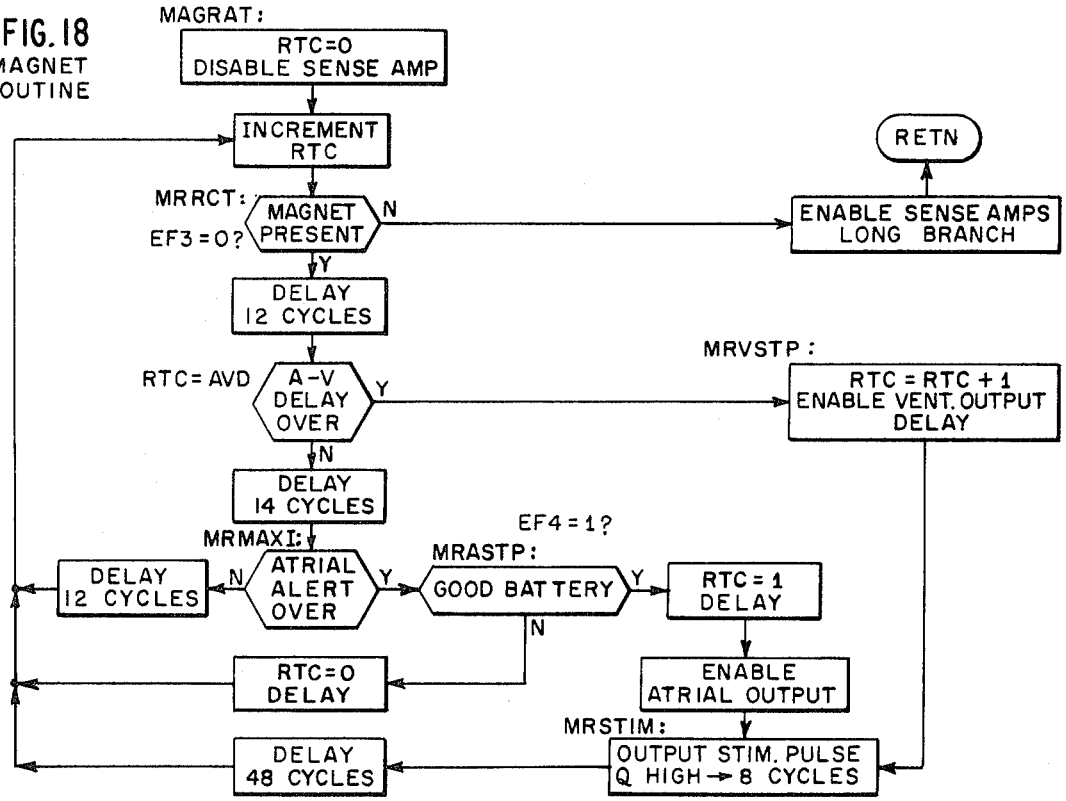
FIG. 18
MAGNET ROUTINE

MULTI-MODE MICROPROCESSOR-BASED PROGRAMMABLE CARDIAC PACER

BACKGROUND OF THE INVENTION

The invention relates generally to cardiac pacers, and more particularly to noninvasively programmable cardiac pacers employing automatic data processing techniques.

The physical characteristics of the human heart lend themselves to various interactive artificial pacing systems. There are two major pumping chambers in the heart, the left and right ventricles. Simultaneously contracting, these chambers expel blood into the aorta and the pulmonary artery. Blood enters the ventricles from the left and right atria, respectively. The atria are smaller antechambers which contract in a separate action which precedes the major ventricular contraction by an interval of about 100 milliseconds (ms), known as the AV delay, approximately one-eighth of the cardiac cycle. The contractions arise from a wave of electrical excitation which begins in the right atrium and spreads to the left atrium. The excitation then enters the atrio-ventricular (AV) node which delays its passage via the bundle of His into the ventricles.

Electrical signals corresponding to the contractions appear in the electrocardiogram. A small signal known as the P-wave accompanies atrial contraction while a much larger signal, known as the QRS complex, with a predominant R-wave, accompanies the ventricular contraction. Ventricular repolarization prior to the next contraction is marked by a small signal in the electrocardiogram known as the T-wave. The P and R waves can be very reliably detected as timing signals by electrical leads in contact with the respective heart chambers.

The typical implanted cardiac pacer operates by supplying missing stimulation pulses on a pacing lead attached to the ventricle. The R-wave can be sensed by the same lead. An additional lead contacts the atrium to sense P-waves, if desired. In AV sequential pacers, discussed below, the atrial lead is also used for atrial stimulation.

One of the problems treated by cardiac pacers is heart block caused by impairment of the ability of the bundle of His to conduct normal excitation from the atrium to the ventricle. It has long been apparent that in treating this form of heart disease it is desirable to base stimulation of the ventricles on the P-wave cycle. This synchronization maintains the heart's normal physiological pacing pattern. Thus, the sino-atrial node, which governs the interval between atrial depolarizations (i.e., the atrial rate) according to the body's needs, controls the artificial ventricular rate in the normal manner.

It is also well known that ventricular stimulation should not be applied during the repolarization period (Q-T) following ventricular contraction for about three-eighths of the cardiac cycle. Stimulation during the Q-T transition can induce undesirable heart rhythms. A spontaneous ventricular beat can arise through normal AV conduction or spuriously as in ectopic ventricular activity. In the latter case, the ventricular beat does not have the normal relationship to atrial excitation.

Various systems for inhibited ventricular stimulation due to spontaneous ventricular signals have been proposed, see for example U.S. Pat. No. 4,386,610 issued June 7, 1983 entitled "Ventricular-Inhibited Cardiac Pacer" by Michael E. Leckrone.

Patients without normal atrial activity, as in symptomatic bradycardia, often have a need for atrial stimulation as well as ventricular stimulation which alone achieves about seventy-five percent of the combined volume flow. AV sequential pacers have been proposed for stimulating the atria and the ventricles. The system in the afore-mentioned patent application, for example, senses and stimulates on both atrial and ventricular leads to provide an atrial-based, AV sequential, ventricular-inhibited pacing mode.

Cardiac pacers are life supporting, theraputic medical devices. They are surgically implanted and remain within a living person's body for years. The vital considerations in cardiac pacing technology tend to dictate a conservative approach, if not reluctance, toward commercially exploiting new developments in electronic circuitry. These tendencies are enhanced by the fact that the relatively simple functional requirements of prior art pacers have been easily implemented using preexisting well-established hardware circuit configurations, the need to avoid excessive heat dissipation, and also by the state of the art in compact batteries which limits current drain to avoid unnecessary replacements which require surgery and reprogramming of an expensive new pacer. The keystone is reliability, followed closely by compactness and low current drain.

In the past, pacers have been implemented by analog or digital timing techniques. Digitally timed pacers having externally programmable pulse parameters have been on the market for several years. For example, the "Omni-Atricor" marketed by the assignee of the present application, Cordis Corporation, employs a reed switch in the implanted pacer which responds to a pulsating magnetic field produced by a magnetic programmer such as Cordis' programmer 222B to program rate, pulse amplitude and other variables. The reed switch is also used to implement a magnet rate mode when a permanent magnet is placed near the pacer causing it to revert to a fixed rate mode in which it will not respond to natural activity.

Stored program data processing devices have been suggested for implants before. See, for example, U.S. Pat. No. 4,424,812 issued Jan. 10, 1984 by Alan Lesnick, entitled "Implantable Externally Programmable Microprocessor-Controlled tissue Stimulator", assigned to the assignee of the present application, which discloses a neural stimulator in which the timing of the pulse rate and pulse width intervals is determined by discrete counter circuits. The programming advantages of single chip general purpose microcomputers are not readily exploitable in the battery-limited cardiac pacer technology of today due to excessive current drain. This is even true of microcomputers based on complementary symmetry metal oxide semiconductor (CMOS) technology such as the RCA CDP 1802 although it does have less current drain.

Microcomputers are, nonetheless, extremely adaptive devices suited by design to making simple as complex logical decisions and taking alternative action. Microprocessor technology presents the challenge of making a pacing routine which monitors sense amplifier outputs indicative of spontaneous activity of the heart and safely determines what type of stimulation would be best suited to the existing condition. It is conceivable that the pacer will diagnose the patient's cardiac function, prescribe the correct stimulation routine and automatically pace the patient's heart accordingly as long as necessary. The chief problem in meeting this challenge is to optimize the software and hardware design as a whole to take advantage of the capabilities of microprocessing while conserving space with a very dense stored program and minimizing current drain in the best practicable way.

The reliability of any digital timing system is keyed to the reliability of the clock circuit which drives it. Crystal oscillators are precise but can have catastrophic failures which must be prevented from producing a life threatening situation. Similarly, weak battery signaling is particularly critical with microprocessors because of their increased current drain. It would also be desirable to treat atrial arrhythmia, but the problem is how to define arrhythmia so that the microprocessor will be able to recognize it, how to treat it when it happens, how to decide when it is over, and how to resume normal pacing.

Ideally, in a microprocessor-based pacer it is desirable to retain the programmability of pacer parameters and to enable preexisting programmers which have already been widely marketed to be used.

One of the problems with pacers which sense on both atrial and ventricular channels is the effect that a stimulation pulse on one channel has on the sense amplifier in the other channel. Ideally the sense amplifier circuit should be designed so that a stimulation pulse on the other channel has no adverse effect on the sense amplifiers.

SUMMARY OF THE INVENTION

These and other objects of the invention have been achieved in an implantable microprocessor-based programmable cardiac pacer which provides physiologically adaptive pacing with one main pacing routine in four fundamental modes: ventricular-inhibited; atrial-synchronized ventricular with or without ventricular sensing; and atrial inhibited, atrial synchronous ventricular inhibited or "AV sequential". In the AV sequential mode, the pacer automatically shifts to atrial synchronous ventricular pacing when the atrial rate exceeds the programmed minimum rate. Temporary pacing modes are available for treatment of arrhythmia and either atrial or ventricular overdrive pacing via chest wall stimulation. The pacer continuously monitors tachyarrhythmia and automatically enters and exits a special arrhythmia response mode.

Stored instruction cycles execute main pacing, arrythmia response, overdrive, magnet rate and programming routines. The programmable parameters are atrial or ventricular pulse widths and sensitivities, maximum, minimum and fall back rates and AV delays. These eight parameters can be altered one at a time or reprogrammed to a standard set in a single programming step using preexisting standard magnetic programmers. The sense amplifiers for the atrial and ventricular channels are under the direct active control of I/O latches addressed by the microprocessor.

Sensed atrial or ventricular activity during "alert" periods steers the main pacing routine through a labyrinth instruction set which cyclically scans the inputs for natural activity. Each scan also increments a "real time clock" which is reset by legitimate atrial activity. The real time clock times the AV delay and maximum and minimum rate intervals. Two other software clocks built into the main pacing routine time ventricular and atrial refractory periods respectively. Premature ventricular contraction sets the real time clock to the AV delay automatically and initiates a ventricular refractory period simultaneously.

The main pacing routine also automatically checks for atrial tachyarrhythmia within its nominal scan cycle. When tachyarrhythmia exceeds a presettable threshold condition, a special arrhythmia routine with ventricular-inhibited pacing is automatically selected. The pacing rate decreases every few seconds until a preprogrammed fall back rate is achieved. After a predetermined interval of normal atrial activity, the pacer returns to the original pacing routine. The scan cycle timing for the main pacing, arrhythmia and magnet rate routines are identical.

A dual clock circuit provides an RC (resistor-capacitor) backup oscillator to the crystal oscillator serving as the clock input to the microprocessor. The backup oscillator is selected either by a battery voltage comparator or by a frequency detector responsive to a catastrophic failure of the crystal. Application of a permanent magnet automatically selects the "magnet rate" routine via the programming routine. The magnet rate pacing mode is normally AV sequential without atrial or ventricular sensing (i.e., asynchronous). A weak battery is signified both by switching over to the lower frequency, voltage-sensitive RC oscillator rate, a hardware function and also by dropping the atrial beat in the magnet rate, accomplished by software.

An automatic blanking system blanks both sense amplifiers during the stimulation pulse and dumps charge at the output amplifier precisely at the end of the pulse. Rate limit is executed both in software and in separate hardware circuits associated with both channels.

To further lower current drain, a split level power supply is used in which as many components as possible, other than the sense and output amplifiers, are powered from the lower voltage bus.

BRIEF DESCRIPTION OF THE DRAWINGS

FIG. 9 is a bit pattern profile of the contents of the read only memory of FIG. 1 at consecutive memory locations in hexadecimal digits.

FIG. 14 is a plan view of the front and back of the program card for use with an existing Cordis Corporation Model 222 or 222B programmer to program the pacer of FIG. 1.

FIG. 15 is a timing diagram of the overdrive mode.

FIG. 16 is a flow chart of the overdrive routine.

FIG. 17 is a timing diagram of the magnet rate mode.

FIG. 18 is a flow chart of the magnet rate routine.

DETAILED DESCRIPTION OF A PREFERRED EMBODIMENT

Figure 1:
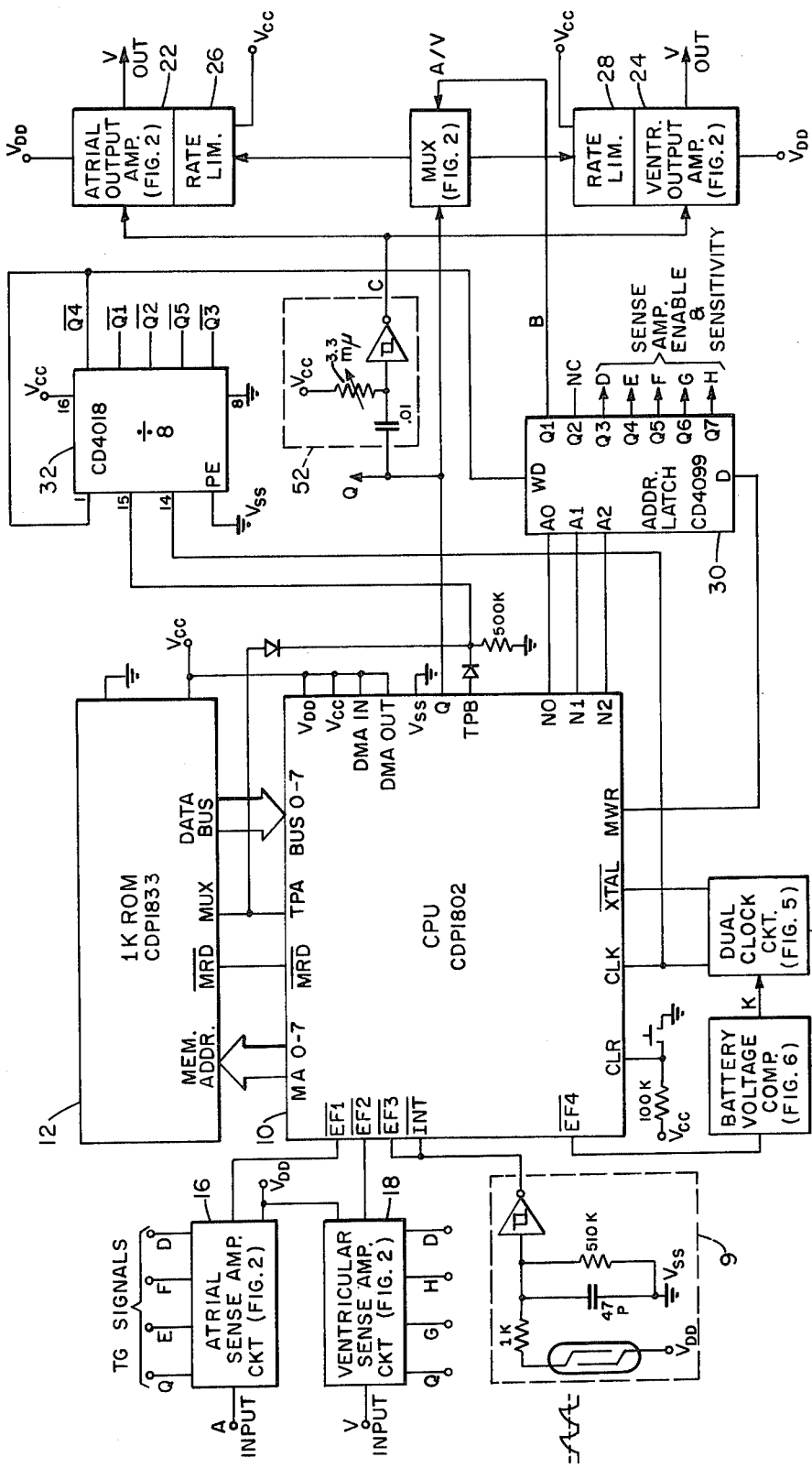
FIG. 1 is a functional block diagram illustrating the electronic circuitry of the cardiac pacer according to the invention.

FIG. 1 illustrates in functional form the overall electronic circuit requirements for pacing and programming in an implantable microprocessor-based multi-mode cardiac pacer according to the invention. The electrical components of the pacer are intended to be powered by lithium compound batteries and sealed together with the battery cells in the customary biologically compatible hermetic enclosure, as in the "Omni Atricor Theta" TM manufactured by Cordis Corporation, the assignee of the present application. The pacer itself is implanted at a suitable location in the human body and is electrically interconnected with a two conductor pacer lead which terminates perveneously in a pair of electrodes situated respectively in the right atrium and bottom of the right ventricle. The electrically conductive case of the pacer forms the return path or ground electrode in a conventional unipolar electrode arrangement.

The pacer shown diagramatically in FIG. 1 is a microprocessor based pacing system with memory and I/O circuits. The heart of the system is a programmed microprocessor or central processing unit (CPU) 10 in FIG. 1. The RCA CDP 1802 COSMAC microprocessor, a single chip CMOS 8-bit bus-oriented CPU, or equivalent is preferred because of its low power consumption and ample internal scratch pad registers. With the exception of the power supply and a few large components such as the crystal discussed below, the entire system is comprised of integrated circuits preferably divided into a pair of hybrids, one primarily for digital circuitry and the other primarily for analog circuitry. The fixed stored program which operates the CPU in accordance with software instructions is in the read only memory, designated ROM 12 in FIG. 1, comprising 1,024 8-bit bytes in a compatible format such as the RCA CDP 1833. When addressed by the memory address bus (MA 0-7) and enabled via the (MRD)-bar output of the microprocessor, the ROM 12 reads a byte from memory out to the microprocessor via the data bus in the conventional manner.

The system is designed so that the CPU 10 is always in operation, that is, the clock input from dual clock circuit 14 is intended to be continuous. The CPU 10, ROM 12 and clock circuit 14 together with the MA and data buses form a microcomputer. The inputs from the outside world are asynchronous since they are not coupled to the clock frequency of the microcomputer. Asynchronous data may be put into the microcomputer in two distinct methods, via "external flag" or "interrupt". The CDP 1802 has four external flag inputs designated as the complements of EF1, EF2, EF3 and EF4. Spontaneous activity in the atria and ventricles is signalled to the microcomputer via the external flag method. External flags are essentially flipflops which may be tested at a particular point in a software routine by a specific instruction. According to the prescribed state of the flip-flop, the instruction may direct the microcomputer to a special branch of the routine. Programming inputs approach the microcomputer as an interrupt (INT)-bar, the other type of asynchronous input. The microcomputer responds to an interrupt by halting whatever software routine it is executing and jumping to a special interrupt service subroutine. The microcomputer returns to the point where it left off after executing the interrupt. Atrial or ventricular stimulation pulses, on the other hand, are provided synchronously by the microcomputer by multiplexing the 1-bit Q output of CDP 1802 which is set for a programmed number of fetch-execute cycles and then reset.

Sensing and Output Amplifier Stages and Blanking

Inputs indicative of spontaneous cardiac activity are provided by separate atrial and ventricular sense amplifier circuits 16 and 18. The atrial lead terminating in the right atrium forms the input to the atrial sense amplifier 16 whose output is applied to (EF1)-bar of the microcomputer. The ventricular sense amplifier input is formed by the ventricular lead which terminates in the right ventricle. The output of the ventricular amplifier circuit 18 is applied to the (EF2)-bar input to the microcomputer.

The output circuit comprises a multiplexor 20 which directs the Q output of the microcomputer to atrial and ventricular output amplifier circuits 22 and 24 via respective rate limit circuits 26 and 28.

The microcomputer does not have an I/O port as it is normally defined in which data is synchronously output via the CPU data bus. The outputs are synchronous but are done without a port. The "pseudo-port" is provided by an addressable latch 30, preferably I/O decoder CD4099. By this latch, sensitivities are selected, output channels are multiplexed and sense amplifier outputs are blanked or the sense amplifiers are turned off completely by software commands. The sense amplifiers 16 and 18 and the multiplexor 20 receive timing or control signals from the addressable latch 30. The addressable latch 30 has eight available outputs, only six of which are used, namely Q1 and Q3–Q7. These outputs correspond to flip-flops which are addressed by 3-bit input from the command bits of the microcomputer, N0, N1 and N2. The command bits are low at all times except when an I/O instruction is being executed. The setting or resetting of the addressed output bit is determined by the state of the D input to the latch 30 which is formed by the (MWR)-bar or "write pulse" of the microcomputer. A sampling gate or "strobe" is provided by the input WD to the latch 30. Because of the intricate timing between the command bits and the write pulse, a counter 32, namely CD 4018, performs a divide-by-eight function utilizing the 32 khz microcomputer clock and two timing pulses TPA and TPB ORed together as the data inputs. The output of (Q4)-bar of the counter 32 forms the input to WD sample gate 30. The usefulness of the latch 30 lies in its ability to retain a particular state at each of its output bits until it is ordered to change by the microcomputer. Thus, the latch operates as an outside register.

Latch 30 tells the multiplexor 20 via line B whether to pass the stimulation pulse to the atrial or ventricular output amplifier 22 or 24. The remaining outputs of the latch, namely D, E, F, G and H operate transmission gates in the sense amplifiers. Line D blanks the output of both sense amplifiers while lines E, F and G, H, respectively, perform input resistance switching for sensitivity selection.

Transmission gates, Schmitt trigger (inverters), and other logic gates are provided by standard RCA CMOS circuits or the equivalent.

Figure 2:
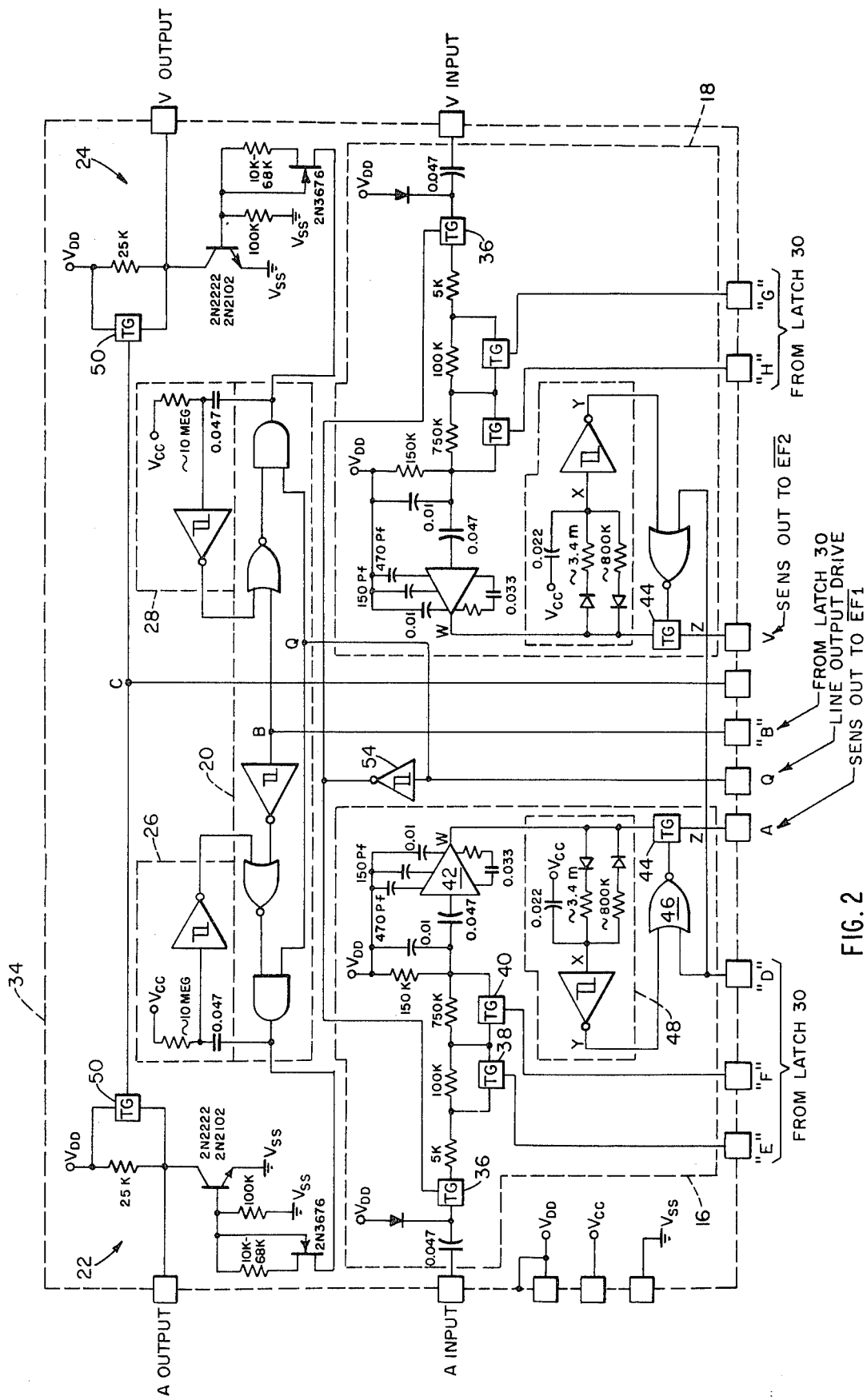
FIG. 2 is an electrical schematic diagram of the analog hybrid circuit containing the atrial and ventricular sense and output amplifier circuits of FIG. 1.

The atrial and ventricular sense output amplifier circuits 16, 18, 22 and 24 along with the multiplexing and rate limiting circuits 20, 26 and 28 for the ouput are incorporated in a single analog hybrid circuit 34 diagrammed in FIG. 2. The sense amplifiers 16 and 18 are symmetrically arranged in the lower half of the circuit diagram of the hybrid 34 while the output amplifier stages 22 and 24 for the atrium and ventricle are at the upper left and right-hand corners of FIG. 22. The electrical components illustrated in FIG. 2 as well as other figures herein where they appear, are illustrated using conventional electrical notation. Values of resistance are given in ohms, for example 1 K meaning 1 kilohm; values of capacitance are given in microfarads unless otherwise indicated. Where two or more values or types are indicated, they are intended to be optional.

Throughout these diagrams the voltages $V_{CC}$, $V_{DD}$, and $V_{SS}$ are consistently used to indicate different nominally fixed levels. Because the pacer of FIG. 1 employs standard off-the-shelf circuitry, the current drain is a constant consideration. One of the ways in which current drain is conserved in this circuit is by creating a second voltage bus to run virtually all of the logic functions, with the exception of the sense amplifiers, noise one-shots and output stages. The nominal battery voltage $V_{DD}$ is 4.26 volts (two-cell lithium battery). The second bus called $V_{CC}$ is nominally 3.5 volts. Since the CDP 1802 and CDP 1833 have a safe operating voltage range which extends below 4 volts, the higher voltage $V_{DD}$ necessary for the amplifier circuits is not essential for the microcomputer, thus, it is replaced by the lower voltage $V_{CC}$. This choice drastically reduces the current drain of the microcomputer system at 32 khz clock rate while preserving full operating characteristics of the amplifier circuits. Sense amplifiers 16 and 18 are internally identical. The lower voltage $V_{CC}$ is not suitable for sense amps because of decreased sensitivity, and would make the output stages more voltage-limited than they now are to deliver 5.5 mA constant-current pulses. Thus they are powered by $V_{DD}$.

The input to sense amplifier 16 from the atrial lead is connected via transmission gate 36 to three serial resistors of progressively larger resistance. After the 5K resistor, interconnected transmission gates 38 and 40 are arranged to shunt the 100 kilohm and 750 kilohm resistors, respectively. The output of the operational amplifier 42 (a custom Intersil Chip No. BL80003Y previously used in Cordis Omnicor pacers) is passed to the (EF1)-bar input of the microcomputer via transmission gate 44 which is controlled by NOR gate 46. The transmission gates 36, 44 at the input and output, respectively, serve blanking functions while the two internal transmission gates 38 and 40 program the finite sensitivities of the amplifier.

In the atrial amplifier 16 the logic signals E and F from the addressable latch 30 determine whether the resistance in the input is 5 kilohms, 105 kilohms or 755 kilohms. Infinite sensitivity is controlled by software by omitting interrogation of the appropriate sense amplifier. The input transmission gate 36 operates to disconnect the input of the amplifier when the Q line is high, that is, when an output stimulation pulse is being applied on either of the leads. The output transmission gate 44 is arranged to disconnect the output when the D line from the latch 30 is high or when noise is sensed by noise one-shot 48. In the presence of noise above about 45 hertz, the one-shot stays high and inhibits pulses from being passed to the CPU.

Figure 3:
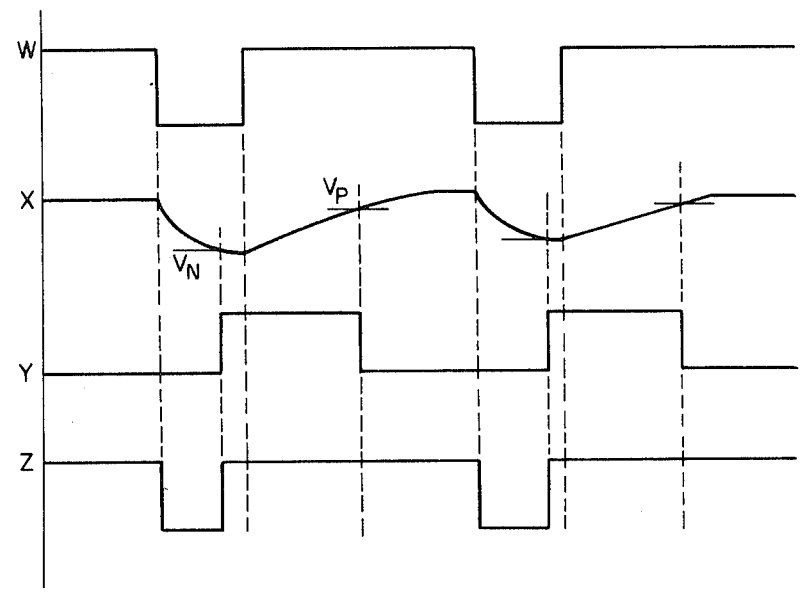
FIGS. 3 and 4 are similar timing diagrams illustrating the response at various points within the sense amplifier circuitry of FIG. 2 to normal and noise sensing, respectively.
Figure 4:
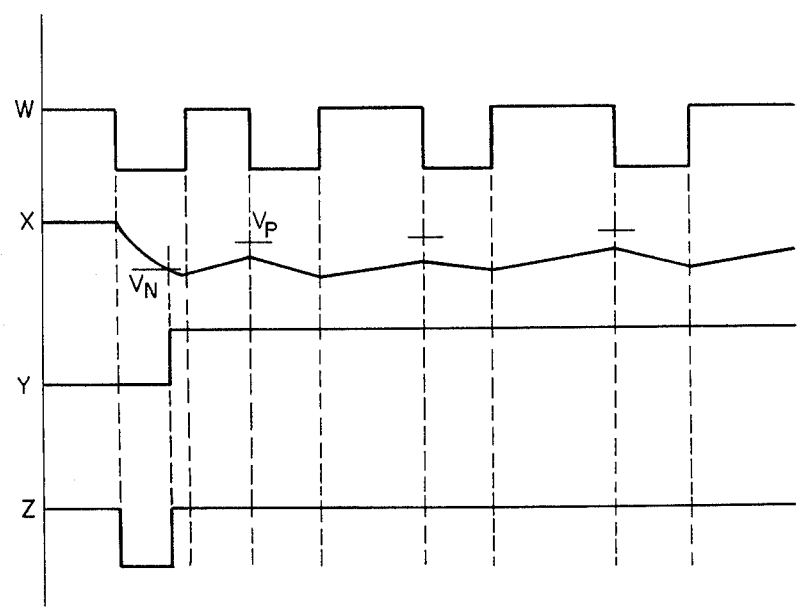

Wave forms appearing in sense amplifier 16 are shown in FIGS. 3 and 4 to illustrate normal response of the amplifier and to block response of the amplifier during noise. Lines W, X, Y and Z in FIGS. 3 and 4 designate corresponding points in the amplifier circuit. $V_p$ is the point at which the output of the Schmidt trigger falls from high to low as shown in line Y. This transition point $V_p$ is not reached when the input signal is too rapid. The result is blocking of the output (Z) as shown in FIG. 4. The output of either sense amplifier is a square pulse of about 20 ms in response to corresponding spontaneous cardiac activity.

Each channel has its own output stage which consists of a constant current controlling JFET and NPN output transistor as shown, for example, for the atrial output amplifier 22 in FIG. 2. The output pulse is amplitude-trimmed to a nominal 5.5 milliamperes (mA) by trimming the JFET feedback resistor. The programmed width of the output pulse determines the intensity of the delivered charge which ranges from 2.75 to 11 microcoulombes per pulse. Pulsewidths are determined in software and come from the CPU via the Q port. The Q signal is switched in accordance with the state of the B signal from latch 30 which controls the multiplexor 20 as shown in FIG. 2. The B signal in the AV sequential mode is addressed and changed by software before each consecutive stimulation pulse.

As a part of the atrial and ventricular halves of the multiplexor 20, a built in rate limiting circuit 26, 28 prevents the pacer from producing stimulating pulses on either channel at a rate faster than approximately 185 beats per minute (bpm). The rate limit circuits 26, 28 are Schmitt trigger retriggerable one-shots which are tuned for approximately 330 ms. Any pulses coming from the CPU at a higher rate will be inhibited. Note that the noise sense and rate limit RC circuits are powered by the lower voltage bus $V_{CC}$ associated with the digital circuitry while the amplifier circuits 16, 18, 22 and 24 are powered at the full battery level $V_{DD}$.

The output of the multiplexor 20 and rate limit circuit 26 on the atrial side, for example, is a logic level 1 which passes through the constant current JFET arrangement to turn on the NPN transistor. The collector, which provides the atrial output stimulation, is connected via a 25 kilohm resistor to $V_{DD}$. The electrically conductive case of the pacer forms a return path for the stimulation pulse and is also connected directly to the battery voltage VDD. In practice a large (10 microfarad) capacitor (not shown) is always connected in series with the atrial output and a voltage limiting (e.g., 8.2 volts) zener diode (not shown) is connected in parallel between the case and the capacitively coupled atrial output. The zener diode protects against defibrillators. The same arrangement is used on the ventricular side. The 25 kilohm collector resistor in the atrial and ventricular output resistors are shunted by respective transmission gates 50. These gates are simultaneously controlled by the C line in FIG. 1. The C signal is produced by a one-shot circuit 52 which is turned on for 20 ms by the falling edge of the Q pulse.

Blanking and charge dumping functions are accomplished by controlling the transmission gates 50 in the output circuit and the transmission gates 36 and 44 at the input and output of the sense amplifiers 16 and 18. When the microcomputer determines that it is time to pulse a chamber, the program jumps to a stimulation subroutine. In the transition, the microcomputer puts a logical "1" (high) on the D line, output Q3 of the addressable latch 30 (FIG. 1). As shown in FIGS. 1 and 2 the D line is connected to operate the transmission gates 44 in the output circuits of both sense amplifiers 16 and 18 simultaneously. Thus when the D line goes high the atrial and ventricular inputs to the microcomputer are disconnected or disabled.

When the CPU "sets Q", one of the output channels begins stimulation as directed by latched B line. The Q line is connected via inverter 54 to transmission gates 36 designed to disconnect the inputs to the two sense amplifiers. As the stimulation pulse begins on one of the channels, both sense amplifiers are disconnected to prevent the output stimulation pulse from charging up the sensing networks in the amplifiers. This enables the amplifiers to recover quickly. Without this arrangement the amplifiers are swamped by the larger signal which has an adverse effect on their recovery or settling time. By completely disconnecting their inputs, the sense amplifiers never see the stimulation pulses.

On the falling edge of the Q pulse, the one-shot 52 (FIG. 1) turns on the transmission gates 50 in parallel with the output pull-up resistors. The charge that is accumulated in the output capacitor (not shown) is rapidly "dumped", thereby allowing the sense amplifiers to recover more quickly due to low offset voltages in the electrolyte.

Meanwhile, on the falling edge of the Q pulse, the sense amplifier input transmission gates 36 are opened to reconnect the amplifiers to the atrial and ventricular leads. Approximately 56 ms after the Q pulse began, the microcomputer tells the addressable latch 30 to reset the D line. This causes the output transmission gates 44 to reconnect the sense amp outputs to the external flags of the microcomputer. The foregoing blanking functions work together to prevent cross talk between channels which could possibly lead to undesirable inhibition of output pulses.

Clock System and Low Battery Indicator

Figure 5:
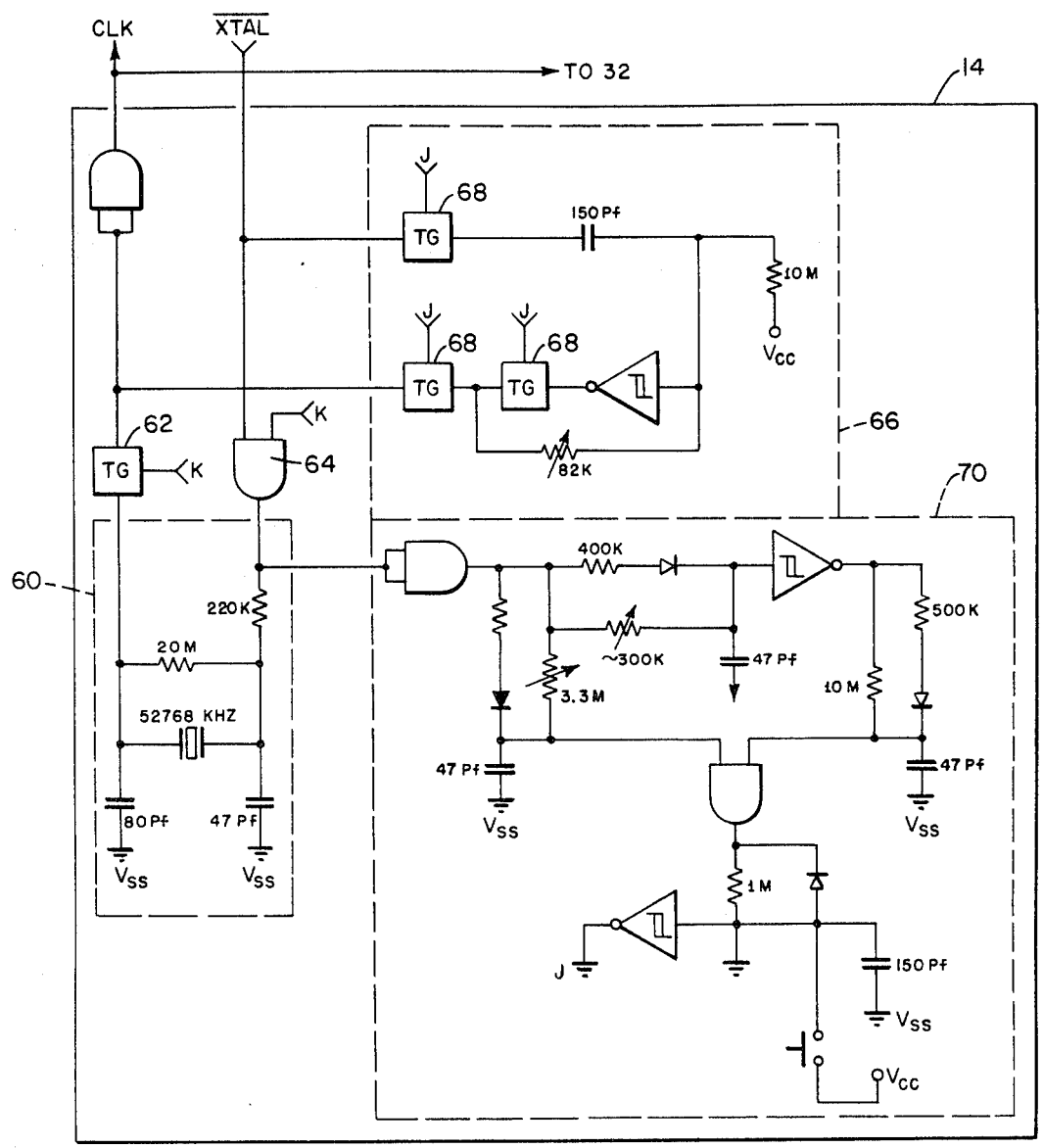
FIG. 5 is an electrical schematic diagram of the dual clock circuit of FIG. 1.

The CPU requires an external oscillator or clock to step it through instruction sequences. The pacer of FIGS. 1 and 2 employs two alternative clocks. As shown in FIG. 5, the dual clock circuit 14 includes a crystal oscillator 60 connected as the main clock to the clock input of the CPU via a normally conducting transmission gate 62. The main clock utilizes a 32.768 khz crystal with stabilizing capacitors. The crystal oscillator can be turned off by the high output of the AND gate 64 whose input is connected to (XTAL)-bar. A backup oscillator is provided by a Schmitt trigger RC oscillator circuit 66 tuned to approximately 31.1 khz at full battery voltage. Note that the oscillator circuit 66 is energized by the lower voltage bus $V_{CC}$, nominally 3.5 volts. A group of three transmission gates 68 serve to enable and connect the RC oscillator to the CPU clock input.

The crystal is an extremely stable oscillating element typically varying by by less than two or three parts per million. However, should the crystal fail for catastrophic reasons such as mechanical shock or excessive moisture, it most probably will either begin oscillating in harmonic multiples of resonance (i.e., 65.536, 98.304 khz, etc.), or it will stop altogether. Such a failure could produce drastic results in pacer performance but is easily detected as a gross change in frequency by the frequency detection circuit 70 in FIG. 5. When the frequency detection circuit 70 senses the crystal oscillator output is outside of the range of about 4 khz to 48 khz, the logic output K and its complement J cause the RC oscillator 66 to be substituted for the crystal oscillator 60. The K signal disconnects the crystal oscillator 60 from the CPU by means of the transmission gate 62 and disables it via the AND gate 64. The J signal activates and connects the RC oscillator 66. This substitution will cause all of the timing functions to be slowed by at least five percent. The slowing factor would be approximately five percent only if the battery was at is full rated voltage since the RC oscillator is voltage sensitive. A variation of this magnitude in the output is easily detected by the physician by observing the magnet rate. Once the RC oscillator is substituted, it will remain in the circuit indefinitely since the frequency detector 70 will find that the crystal oscillator output is zero, i.e., outside the acceptable range.

Figure 6:
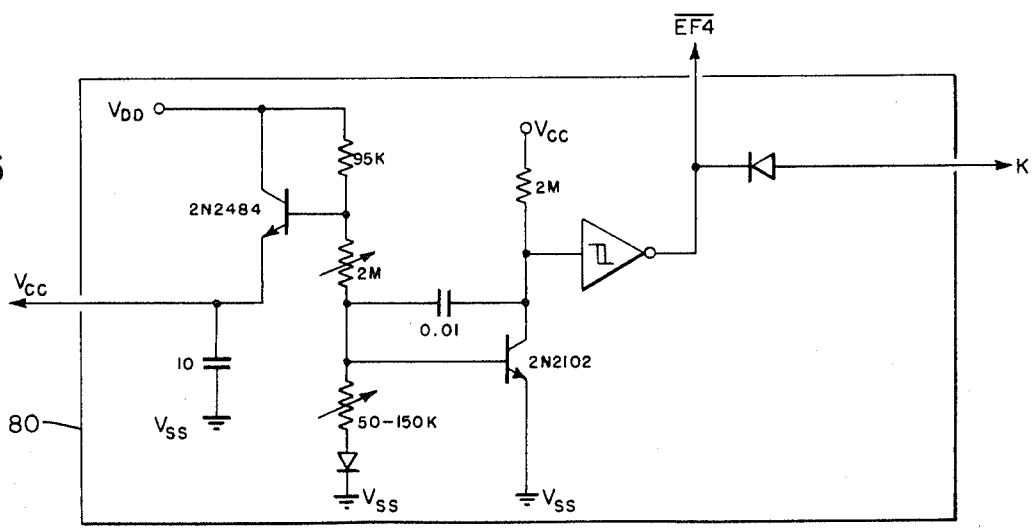
FIG. 6 is an electrical schematic diagram of the battery voltage comparator circuit of FIG. 1.

The logic K signal can also be produced by the battery voltage comparator 80. As shown in FIG. 6 the comparator circuit 80 comprises a critically biased transistor circuit and a Schmitt trigger 84. The emitter of the first NPN transistor (2N2494) serves to energize the $V_{CC}$ bus. The second transistor (2N2102) is biased in such a way that it is conducting at 4.26 volts and thereby presents a low input to the Schmitt trigger. When the battery voltage $V_{DD}$ falls to about 3.85 volts between first and second plateaus of the discharge profile, this biasing network shuts the second transistor off (not conducting) and the Schmitt trigger output goes from high to low. As the Schmitt trigger goes to an external flag (EF4)-bar of the CPU, the microcomputer can determine when the battery voltage is low and act accordingly in the magnet rate. In addition, the output of the Schmitt trigger produces a K signal which is phantom ORed with the K signal from the frequency detector circuit 70. This signal from the battery voltage comparator causes the main crystal oscillator to be disconnected from the clock input and disables the main oscillator via the AND gate 64. Since the frequency detector 70 senses that the crystal oscillator is off, it also presents the J logic output which activates the RC oscillator 66.

Figure 7:
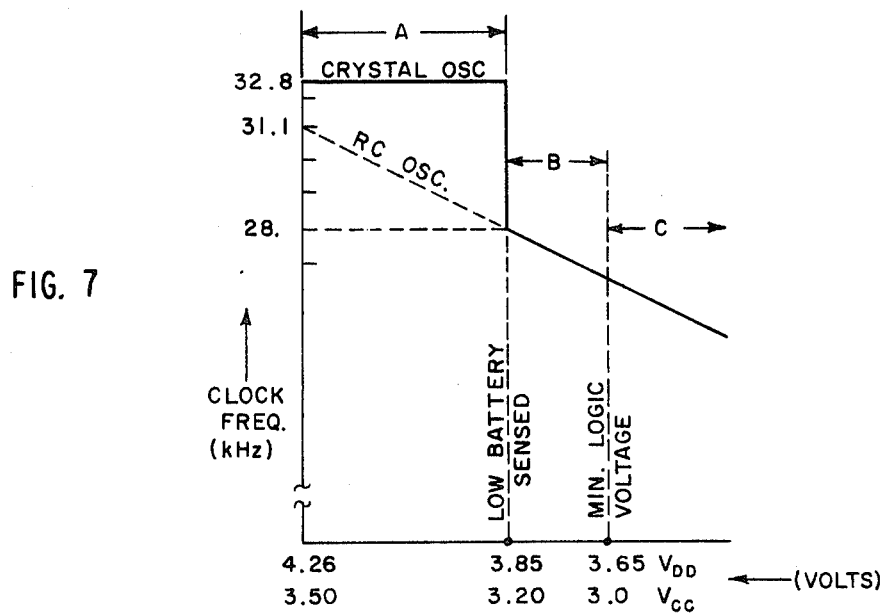
FIG. 7 is a graph of clock frequency versus declining battery voltage.

As shown in FIG. 7 the battery voltage circuit 80 causes the clock frequency for the microcomputer to fall from the nominal 32.8 khz value to the output frequency of the RC oscillator when battery voltage $V_{DD}$ is below 3.85. This produces about a fifteen percent drop in the output frequency. In the good voltage region designated A in FIG. 7, where the battery voltage $V_{DD}$ is above 3.85 volts, the crystal oscillator frequency will govern the microcomputer unless there is a catastrophic failure. If the crystal oscillator frequency is outside of the acceptable range and the battery voltage is still in range A the RC oscillator will be switched in at 28 to 31 Khz depending on the battery voltage level. As the voltage decreases from 3.85, the microcomputer is operated by the RC clock. The battery voltage eventually reaches a point where the low voltage bus $V_{CC}$ for digital circuits is below 3.0 volts, the minimum safe operating voltage for the CDP 1802 thus there is defined a second region B for low battery operation with the RC oscillator. Below region B a third region C exists where the battery voltage is insufficient to ensure viable operation of the microcomputer at the available clock frequency.

In the dual clock circuit 14 as shown in FIG. 5 the frequency detection circuit 70 has a pushbutton switch which is used to start the crystal oscillator at the factory. The push-button switch merely symbolizes the application of a voltage level and is done during final assembly and testing by momentarily jumpering the K output of the frequency detector to the $V_{CC}$ bus. The CPU is initialized at the factory in a similar manner by momentarily grounding the clear terminal as indicated in FIG. 1.

Programming is accomplished via a reed switch circuit 90 (FIG. 1). An RC filter network and a Schmitt trigger help shape the programming pulses. The external programmer is an electromagnetic impulse programmer (not shown) which produces a saw tooth flux versus time waveform as shown to the left of circuit 90 in FIG. 1. The dashed line represents the threshold level at which the reed switch contacts close. This level is dependent of course on the proximity of the external programmer to the pacer. The Schmitt trigger output goes to the interrupt terminal and external flag (EF3) inputs of the CPU, where software then decodes and accepts or rejects programming codes. The software bandpass frequency is designed for nominal 330 hertz programming pulses which fall within a range of 227 to 512 hertz. Besides the electromagnetic programmer, the reed switch is also responsive to a permanent magnet. If the external flag (EF3)-bar stays high for a longer period of time than it would normally stay high for programming pulses, the CPU assumes that a permanent magnet has been applied and goes into the "magnet rate" routine which provides fixed rate AV sequential stimulation unless the battery is below 3.85 volts, in which case, by testing (EF4)-bar, the magnet rate mode drops the atrial beat. Except for the reed switch, the crystal and the analog hybrid circuits 16 through 28 (FIG. 2), all of the circuitry in FIG. 1 is preferably included in a single digital hybrid.

Parameters

Table I gives the nominal parameter values of the pacer of FIG. 1.

TABLE I

|  | Nominal Values | Values in Std. Mode |
|---|---|---|
| Output current, mA (not programmable) | 5.5 | 5.5 |
| Output Voltage, V | 4.2 | 4.2 |

TABLE I-continued

|  | Nominal Values | Values in Std. Mode |
|---|---|---|
| (open circuit) | | |
| Refractory period, ms (atrial or refractory) (not programmable) | 312 | 312 |
| AV Delay, ms | 80 | 120 |
|  | 120 | |
|  | 165 | |
|  | 250 | |
| Minimum pacing rate, ppm (fixed rate) | 50 | 70 |
|  | 60 | |
|  | 70 | |
|  | 80 | |
| Maximum atrial synchronous | 100 | 160 |
|  | 130 | |
|  | 160 | |
|  | 180 | |
| Fall back rate, ppm | 55 | 75 |
|  | 65 | |
|  | 75 | |
|  | 85 | |
| Ventricular Sensitivity, mV | 0.8 | 1.5 |
|  | 1.5 | |
|  | 2.5 | |
|  | Off | |
| Atrial Sensitivity, mV | 0.8 | Off |
|  | 1.5 | |
|  | 7.0 | |
|  | Off | |
| Ventricular pulse duration | 0.5 | 1.5 |
|  | 1.0 | |
|  | 1.5 | |
|  | 2.0 | |
| Atrial pulse duration, ms | Off | Off |
|  | 0.5 | |
|  | 1.0 | |
|  | 1.5 | |

The software is designed to automatically start the pacer off in the ventricular-inhibited (VVI) mode with "standard values" indicated in Table I. The output current and voltage are fixed. Refractory periods when the output of the sense amplifier is ignored are both fixed and identical.

There are four distinct modes of operation, as indicated in Table II below: ventricular-inhibited (VVI), atrial-synchronous ventricular-inhibited (VAT delta+VVI), atrial-synchronous without ventricular-inhibited (VAT delta) and atrial-inhibited, atrial synchronous ventricular-inhibited (DDI). The symbol "x" indicates that the variable parameter is programmed to a finite value.

TABLE II

| Parameters | VVI | VAT + VVI | VAT | DDI (AAI + VAT + VVI) |
|---|---|---|---|---|
| Atrial Output Pulse Duration | Off | Off | Off | x |
| Atrial Sensitivity | Off | x | x | x |
| Ventricular Output Pulse Duration | x | x | x | x |
| Maximum Rate | NA | x | x | x |
| Fall Back Rate | NA | x | x | x |
| A-V Delay | NA | x | x | x |
| Ventricular Sensitivity | x | x | Off | x |
| Minimim Rate | x | x | x | x |

Timing

Figure 8:
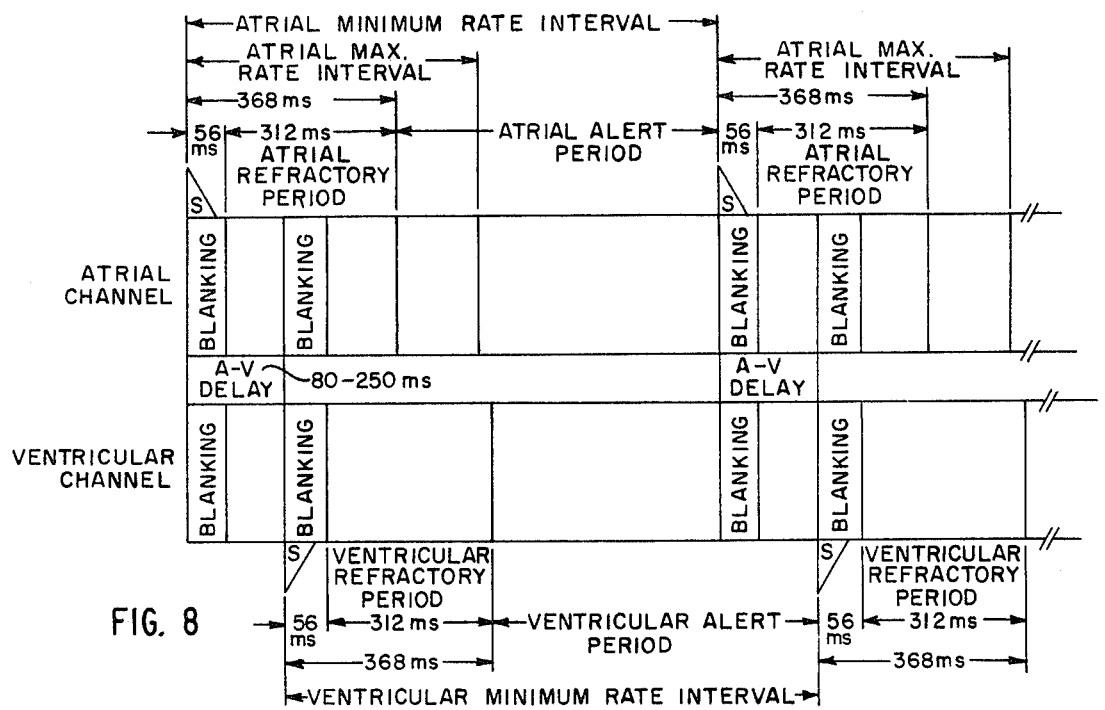
FIG. 8 is a timing diagram illustrating the atrial and ventricular timing cycles which characterize the main pacing routine.
Figure 10:
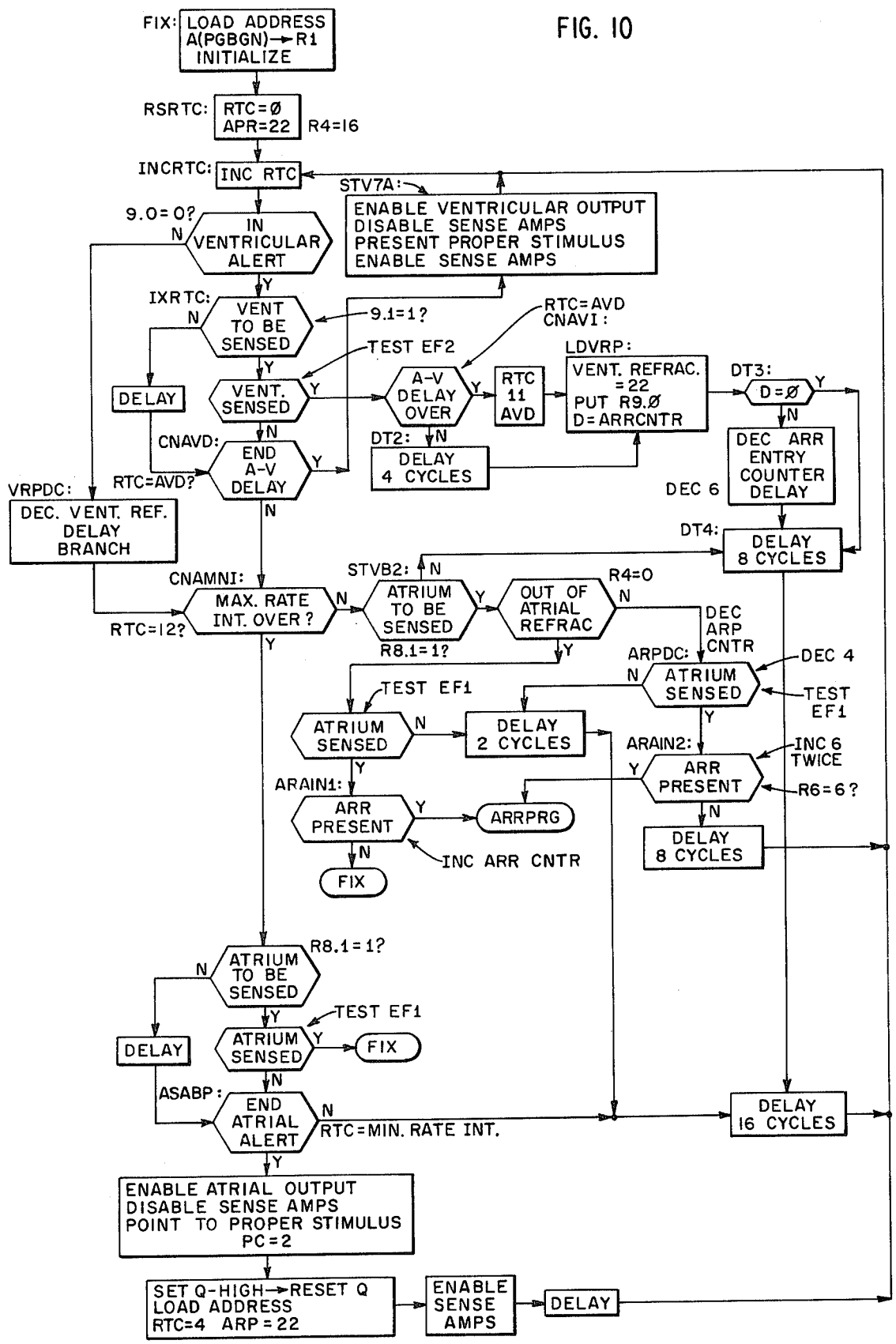
FIG. 10 is a flow chart of the main pacing routine.

FIG. 8 sets forth the basic timing relationships employed by the main pacing routine of FIG. 10. The minimum rate interval is the pulse-to-pulse interval in the minimum programmed rate. When the spontaneous atrial rate decreases below this rate as in bradycardia, the pacer will stimulate the atria at the minimum programmed rate (e.g. 70 bpm) when programmed for the AV sequential mode (DDI). The full AV sequential mode in bradycardia and heart block illustrates the case when slow or absent atrial and ventricular activity calls for stimulation on both channels.

The timing cycle for each channel consists of a refractory period and an alert period. The refractory periods are both fixed at 312 ms and occur after sensed or stimulated activity. During the refractory period, the affected channel cannot respond to any input received. However, the pacer can count the number of atrial contractions which occur during the programmed maximum rate interval for use in determining atrial tachyarrhythmia.

Atrial or ventricular stimulation causes 56 ms blanking via the D line (FIGS. 1 and 2) in both channels. The AV delay is timed by software. If the programmed AV delay elapses before spontaneous ventricular activity, the ventricules are stimulated. After the blanking period, the CPU commences a ventricular refractory period. Meanwhile, in the atrial channel the expiration of the atrial refractory period begins the atrial alert period in which the CPU monitors the atrial lead for a P-wave. If the entire minimum rate interval goes by without sensing a P-wave, the CPU stimulates the atria. After blanking, the ventricular alert period resumes sensing. If no ventricular activity appears by the end of the next AV delay, the CPU issues a ventricular pulse. If normal AV conduction occurs resulting in ventricular contraction before the end of the AV delay, the ventricular output is inhibited and the ventricular channel becomes refractory.

The maximum rate interval only applies to the atrial channel. It places a ceiling on the rate of natural atrial activity. If atrial pulses are so fast that they regularly precede the maximum rate interval, the pacer automatically enters the "arrhythmia mode".

Software

The real life identity of the pacer of FIG. 1 is found in the software contained in the program memory. Each byte in ROM 12 is conventionally represented by two hexadecimal "hex" digits. FIG. 9 shows the contents of ROM 10 in groups of four hex digits representing two bytes of memory at neighboring memory locations. Memory locations are arranged consecutively row by row from right to left and top to bottom. Most of the ROM bytes are instructions from the standard repertoire of the CDP 1802 system; some of the bytes represent data or parameters. All of the ROM bytes are fixed; they can only be read, not changed.

The sixteen 16-bit internal registers within the CDP 1802 are used for variables. Table III below contains a list of the register assignments, the registers being indicated by hex code from zero through F. For example, "8.1" and "8.0" designate the high and low bytes of register 8, respectively.

TABLE III

R0 = Main program counter
R1 = Interrupt pointer
R2 = Pointer to stimulus routines/scratch pad
R3 = Scratch pad
R4 = Atrial refractory period (ARP)
R5 = Fallback interval count/real time clock (RTC)
R6 = Arrhythmia status/arrhythmia counter (ARR)
R7 = Programming pulse counter (PPC)

TABLE III-continued

R8 = R8.1 atrial sense enable,
    R8.0 real time clock (RTC)
R9 = R9.1 ventricular sense enable,
    R9.0 ventricular refractory period (VRP)
RA = Atrial stimulus pointer (main pacing routine) (AST)
RB = Ventricular stimulus pointer (main pacing routine) (VST)
RC = Maximum rate interval (max)
RD = Minimum rate interval (min)
RE = Fallback rate interval (FBR)
RF = A-V delay In addition to the "initialization" instructions, the pacer program includes five distinct major routines for main pacing, arrhythmia, programming, overdrive and magnet rate.

Initialization

The pacer has no on/off switch as such. When the batteries are installed and the CPU has been cleared and the oscillator started, the CPU automatically begins executing instructions from the address 0000. The computer proceeds to initialize the 16 internal registers for ventricular-inhibited pacing with the standard parameter values. The pacer at this point has not been externally programmed. It starts off in the VVI mode at 70 bpm. The initialization routine disables the atrial sense amplifier by loading the byte "10" (hex) into the data register and then transferring it to R8.1. Ventricular sensitivity is selected by instructions which reset the G line (Q6) from the addressable latch 30 in FIG. 1 and set the H line (Q7) of the latch to determine the input resistance of the ventricular sense amplifier in FIG. 2. The address of the appropriate "standard stimulation routine" for 1.5 ms pulsewidth is loaded into RB. Since in the VVI mode no atrial stimulation is needed, the address of a "dummy" stimulation routine is loaded into atrial stimulation pointer RA. Next, zeros are loaded into the following registers: 6, 7, 9, A.1, C.1, D.1, E.1 and F.1. Next RC.0 is loaded with the address of the maximum rate (160 bpm), RD.0 is loaded with the address of the minimum rate (70 bpm), RE.0 is loaded with the address of the fall back rate (75 bpm), and RF.0 is loaded with the address of the standard AV delay (120 ms). The program immediately enters the main pacing routine having set up standard parameters during initialization.

Main Pacing Routine

The main pacing routine runs the pacer. It can execute any one of the four basic pacing modes. It is responsible for timing the refractory periods, the AV delay, the maximum rate and minimum rate intervals. It tests for atrial and ventricular activity if so programmed, determines whether or not to execute atrial or ventricular stimulation pulses. Except in VVI it keeps track of the number of atrial pulses sensed during the maximum rate interval and determines whether or not to exit the main pacing routine and go to the arrhythmia routine. There are three time keepers in the main pacing routine: the real time clock (RTC) implemented by regularly incrementing R8.0; the ventricular refractory period register R9.0, and the atrial refractory period register R4. Registers R9.0 and R4 are loaded and decremented. Starting at the "FIX" location (FIG. 10), the CPU loads the address of the interrupt service routine for programming and enables the interrupt system. The program then proceeds to location "RSRTC"

standing for reset real time clock, which it does and then initializes the atrial refractory period by placing the hex number 16 in R4.

At location "INCRTC" the real time clock is incremented by one. This instruction begins a "scan" cycle. From this point in FIG. 10 there is a labyrinth of decision loops all of which return to INCRTC, some of them by way of the "FIX" location. No matter what path is taken, instructions which must be executed along the way are designed to take exactly 58 machine cycles or 14.1 ms at the crystal clock frequency. The only exception to this rule is legitimate atrial activity which resets RTC and reloads R4. This 14 ms period represents the fundamental scan time or time "window" during which the CPU looks for outside activity. The refractory periods 312 ms take 22 scans (16 hex). After incrementing the real time clock, the CPU next determines whether the pacer is in the ventricular refractory period. By testing the ventricular refractory register 9.0. The question "in ventricular alert?" corresponds to an instruction which calls for the routine to branch to a different loop if R9.0 is not yet zero. During initialization R9.0 was set at zero. Thus the pacer starts off in ventricular alert. Next, having found that it is in ventricular alert, the computer asks if the ventricules are to be sensed by inquiring whether R9.1 is "1" or zero. If it is "0" the ventricular sense amp is on, in which case the CPU next tests (EF2)-bar for ventricular activity. If there is no ventricular activity, the main routine proceeds to determine whether it is precisely the end of the AV delay period by seeing whether RTC equals AVD. If it does and no ventricular activity has been sensed, the program jumps to the location STV7A to produce a ventricular output according to the programmed pulse width.

The CPU prepares for ventricular stimulation by first selecting channels and disabling sense amplifiers via the B and D lines of the addressable latch 30. Next, the address of the ventricular stimulation program selected in accordance with desired pulsewidth is retrieved from RB and put in to the scratch pad R2. With the instruction "SEP 2", the CPU designates R2 as the program counter. Accordingly, the program jumps to the address stored in R2, i.e., the address of the ventricular stimulation pointer transferred from RB. In standard mode the address of the routine which produces a 1.5 ms pulse was loaded into register B. The program now jumps to this address where the CPU finds the 1.5 ms ventricular stimulation subroutine which starts off by setting Q for three fetch-execute cycles corresponding to 1.5 ms and then resetting Q and branching to "MVSTP". R2 as the program counter is incremented after each instruction is executed. At location MVSTP the program prepares to return to the main pacing routine by placing a zero in RO.1 and loading the address of instruction INCRTC in RO.0. Next the number 4 is placed in the RTC (R8), the ventricular refractory period is initialized by placing the hex number 12 (4 away from 16) in R9. The program proceeds to load the hex digits 1F into the scratch pad R3 and decrement it to zero so as to delay 190 machine cycles, decrementing the arrhythmia counter (R6) if it is not zero, and then setting the Q3 latch which re-enables the sense amps to end the 56 ms blanking and finally executing the instruction "SEP 0" (line 539) which redesignates R0 as the program counter. Since R0 has already been loaded with the address of the instruction INCRTC, the computer turns back to the beginning of the main pacing routine.

If the RTC had indicated that it was still before the end of the AV delay, the routine at location CNAMI would next ask whether the pacer was already beyond the maximum rate interval by subtracting the present value of RTC (R8.0) from the programmed value of maximum rate interval (RC). If the time from the last atrial pulse is less than the maximum rate interval, the CPU proceeds to location STV82 to determine whether the atrium is to be sensed by seeing whether R8.1 contains a "1". Atrial sensing is disabled in the VVI mode and the routine would return via delays to INCRTC. If it is not disabled, the CPU proceeds to question whether the atrial refractory period is over by seeing whether R4 has been decremented to zero yet. If the pacer is still in atrial refractory, R4 is decremented and the atrial lead is checked by testing EF1. If atrial activity has been sensed, it is considered to be an arrhythmia and the arrhythmia counter R6 is incremented twice. If, after incrementing, R6 holds a number greater than or equal to six, the pacer exits the main pacing routine and jumps to the special arrhytmia routine ARRPRG. If R6 is not six yet, the pacer returns to INCRTC.

The other branch of the test for atrial refractory is chosen if the atrial refractory period has expired (R4=0 and still within maximum rate interval). In this case R4 is not decremented but if the atrium is sensed by testing EF1, R6 is incremented twice, tested to see if it is six yet, and if not the pacer returns to INCRTC via FIX to reinitialize the atrial refractory period, the period having elapsed.

If the maximum rate interval is found to have been exceeded, then from CNAMNI the CPU continues downwards (FIG. 10) checks R8.1 to see whether the atrial sense amp is enabled, and then tests EF1 to see if the atrium has been sensed. If it has, the CPU goes to FIX, resets the RTC to zero and reinitializes the atrial refractory period (R4=16) and resumes the main pacing program via INCRTC.

If the atrial sense amp has not sensed atrial activity, then instead of returning to FIX, the pacer proceeds to ask whether the atrial alert period is ended, i.e. does RTC equal the minimum rate interval. If it does, then an atrial stimulation routine is begun. Atrial stimulation is achieved in the same way as ventricular stimulation by first blanking the sense amplifiers and then changing the designation of the program, so that the address of the stimulation program will turn up. During the atrial stimulation routine the real time clock is reset to four at the atrial refractory period counter is reset to hex 16 before returning to INCRTC. In atrial-synchronous modes lacking atrial stimulation, the atrial stimulation routine is a dummy.

In the instruction following INCRTC, if the ventricular refractory register 9.0 is not zero yet, the steps which cause the ventricular sense amplifier to be interrogated are skipped, the ventricular refractory period register is decremented and a delay instituted to take up the same amount of time that the ventricular sense amp interrogation would have taken.

If the ventricular refractory period register has already been decremented to zero and thus the pacer is in ventricular alert, and ventrical activity is sensed, the routine brances to CNAVI to test whether RTC is greater than AVD. This determines whether the sensed ventricular activity is legitimate or a PVC. Whether the AV delay is past or not, the ventricular refractory period register 9.0 is reinitialized to hex 16, the arrhythmia counter R6 is decremented if it is not zero and the pacer returns to INCRTC. If the RTC indicates that the AV delay has since passed, the ventricular activity is a premature ventricular contraction. In this case the RTC is set to the programmed AVD to reset the timing so as to provide a compensatory gap before the next atrial stimulation is due.

Arrhythmia Routine

By incrementing the arrhythmia counter twice whenever atrial activity is sensed before the expiration of the maximum rate interval and decrementing it once whenever ventricular activity is sensed or stimulated, the arrhythmia counter makes a weighted value judgment to classify atrial tachyarrhythmia. Three fast atrial beats with no interceding ventricular pulses will call the arrhythmia routine; however, two fast atrial beats, assuming the arrythmia counter started at zero, followed by a ventricular pulse will require two more premature atrial beats in order to exceed the threshold.

If atrial tachycardias persist and are sensed, arrhythmia register (R6) will soon accumulate six. For example, if one atrial tachyarrhythmia pulse were sensed during the cardiac cycle and this condition persisted for six cycles, the arrhythmia counter would be full. Similarly, if two tachycardia pulses occurred during the maximum rate interval it would take three cardiac cycles before the arrhythmia counter reached six. On the other hand, if there were two atrial tachyarrhythmias sensed in one cardiac cycle followed by four cardiac cycles without arrhythmia, the arrhythmia counter would be completely cleared.

Figure 11:
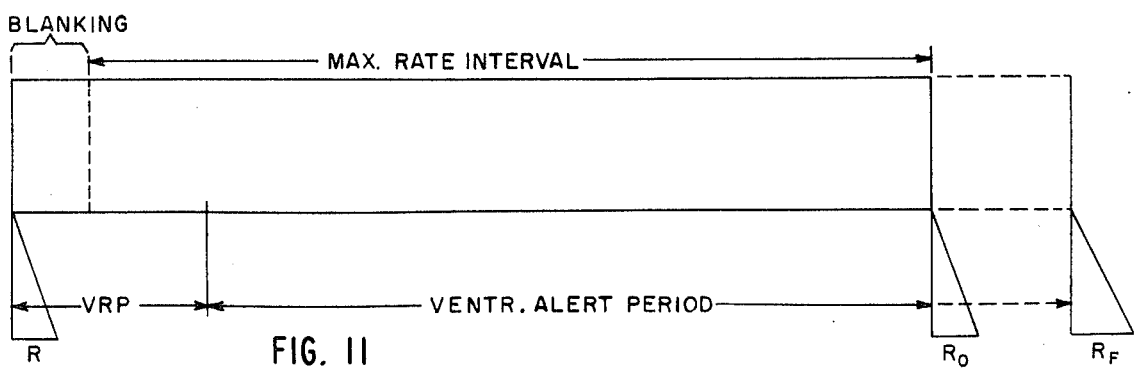
FIG. 11 is a timing diagram of the tachyarrhythmia response mode.
Figure 12:
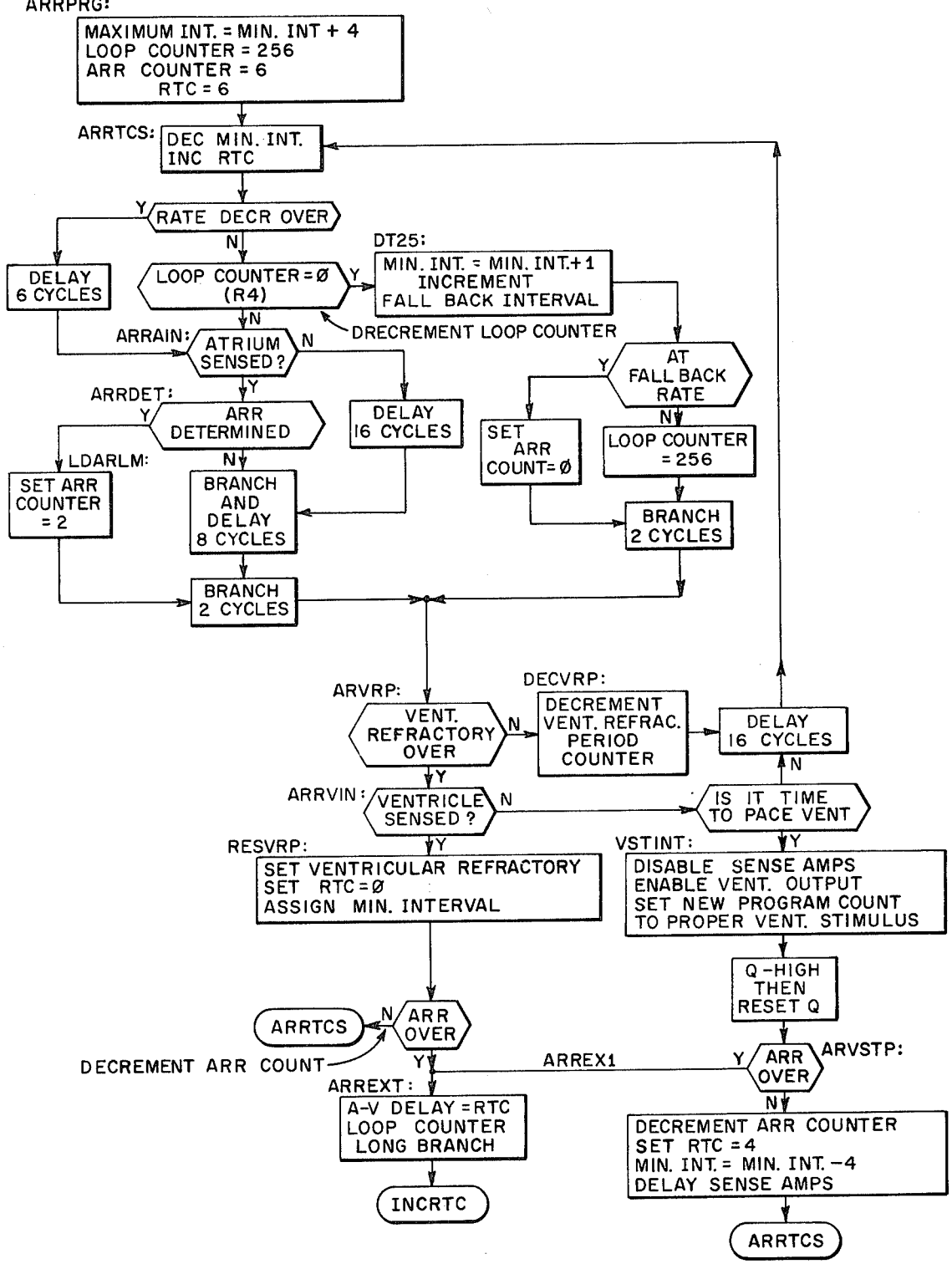
FIG. 12 is a flow chart of the arrhythmia routine.

In any event, when R6 reaches six, the CPU automatically jumps to the beginning address of the tachyarrhythmia response subroutine shown in FIGS. 11 and 12. The object of this routine, as shown in the timing diagram of FIG. 11, is to change the pacing mode to a fast ventricular inhibited (VVI) pacing mode slightly below the programmed maximum rate e.g. 160 bpm and gradually decrease the rate (i.e. increase the escape interval) to the programmed fall back rate e.g. 75 bpm. In FIG. 11 the initial fast VVI interval corresponds to R to $R_0$ while the ultimate fall back rate corresponds to R to $R_F$.

The arrhythmia routine begins at memory location 349 in hex digits. At the start of this routine location "AARPRG", the CPU goes through a number of instruction which initialize the registers. In particular, RC holding the maximum rate interval is transferred to the low byte of R5 plus a count of 4 equivalent to 56 ms (4 times 14 ms). Next a loop counter, low byte of register R4, is loaded with all "1"'s equivalent to 256 or "FF" in hex code; and the arrhythmia counter (R6) and real time clock (R8.0) are set at six. At "ARRTCS", FIG. 12, the CPU begins the tachyarrhythmia routine scan. This scan routine is also 58 machine cycles long and each scan will take 14.1 ms to complete. In this routine, the pacer is disassociated from the atrium (although atrial activity is monitored) and paces purely as a VVI device, initially at the maximum rate interval plus 56 ms.

Gradual rate decrease is accomplished by decrementing the loop counter (which starts at 256) during each scan. After 256 scans, when zero is reached, at location DT25 the interval between the ventricular stimulation pulses is incremented by one by adding a binary "1" to R5, the fall back interval counter. Within this scan routine, the ventricular sense amplifier is interrogated in the same manner as it was in the main pacing routine.

The timing cycle in this routine is based upon ventricular activity, so that sensed or induced ventricular activity resets the RTC at the program location "RESVRP". The ventricular refractory period is the same here as in the main pacing routine.

Tachyarrhythmic atrial activity continues to be monitored during the arrhythmia routine by seeing whether atrial signal is present at EF1 prior to expiration of the programmed maximum rate interval. This time period is determined as usual by comparing RTC with the number stored in register RC. When sensed atrial activity falls within this window, it is assumed to be faster than the programmed maximum rate and the number two is loaded into the arrhythmia register. As long as this atrial tachyarrhythmia is sampled within the maximum rate interval window, the number 2 will be entered into the register each time. Whenever ventricular activity is sensed or induced at program location ARRVIN, the arrhythmia routine tests whether the arrhythmia counter is at zero. If it is not at zero it decrements the arrhythmia register and returns to the top of the arrhythmia routine (ARRTCS). If it is at zero the program jumps back to the main pacing routine at INCRTC, first setting the RTC equal to AVD as in the PVC response. When the CPU reaches the programmed fall back rate, assuming that it stays in the arrhythmia routine long enough, it will continue to operate as a VVI pacer at the fall back rate indefinitely. However, once the fall back rate has been achieved, new fall back rate cannot be instantly programmed. The CPU will not honor the request until it once again enters the arrhythmia routine.

Like the main pacing routine the arrhythmia routine has its own stimulation subroutines at hex location 375 program location VSTINT.

Programming Routine

Figure 13A:
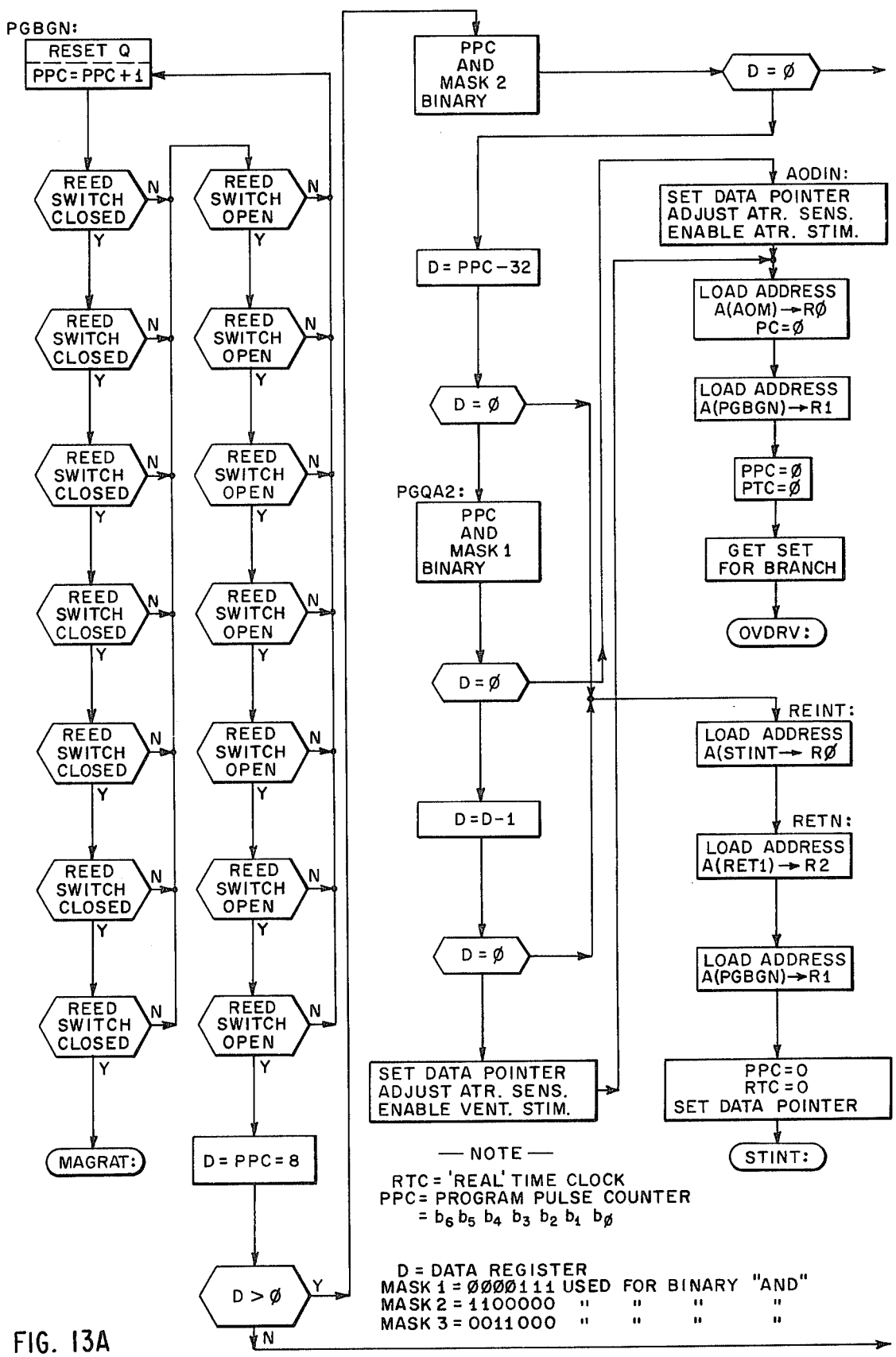
FIGS. 13A, 13B and 13C represent a flow chart of the programming routine.
Figure 13B:
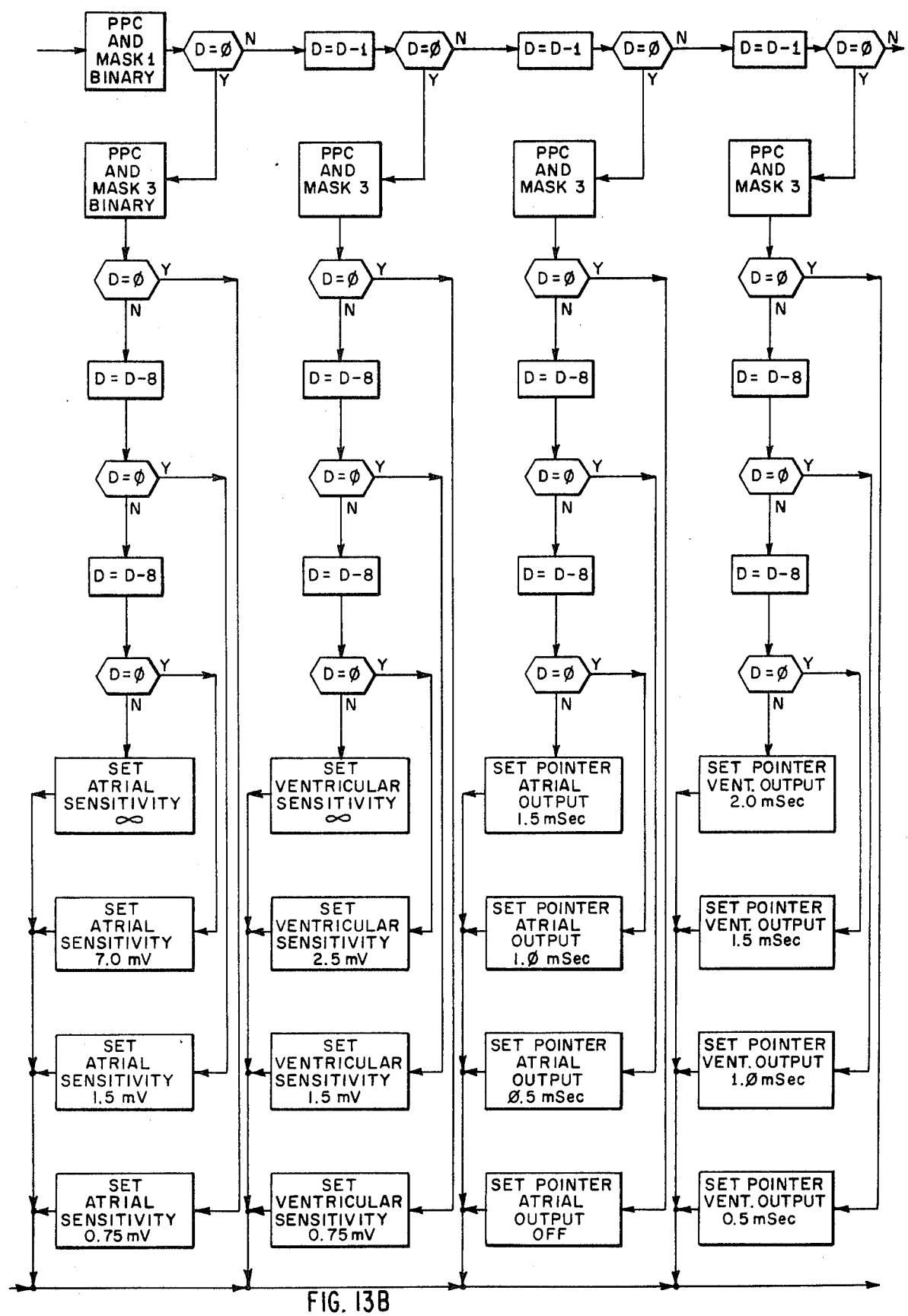
Figure 13C:
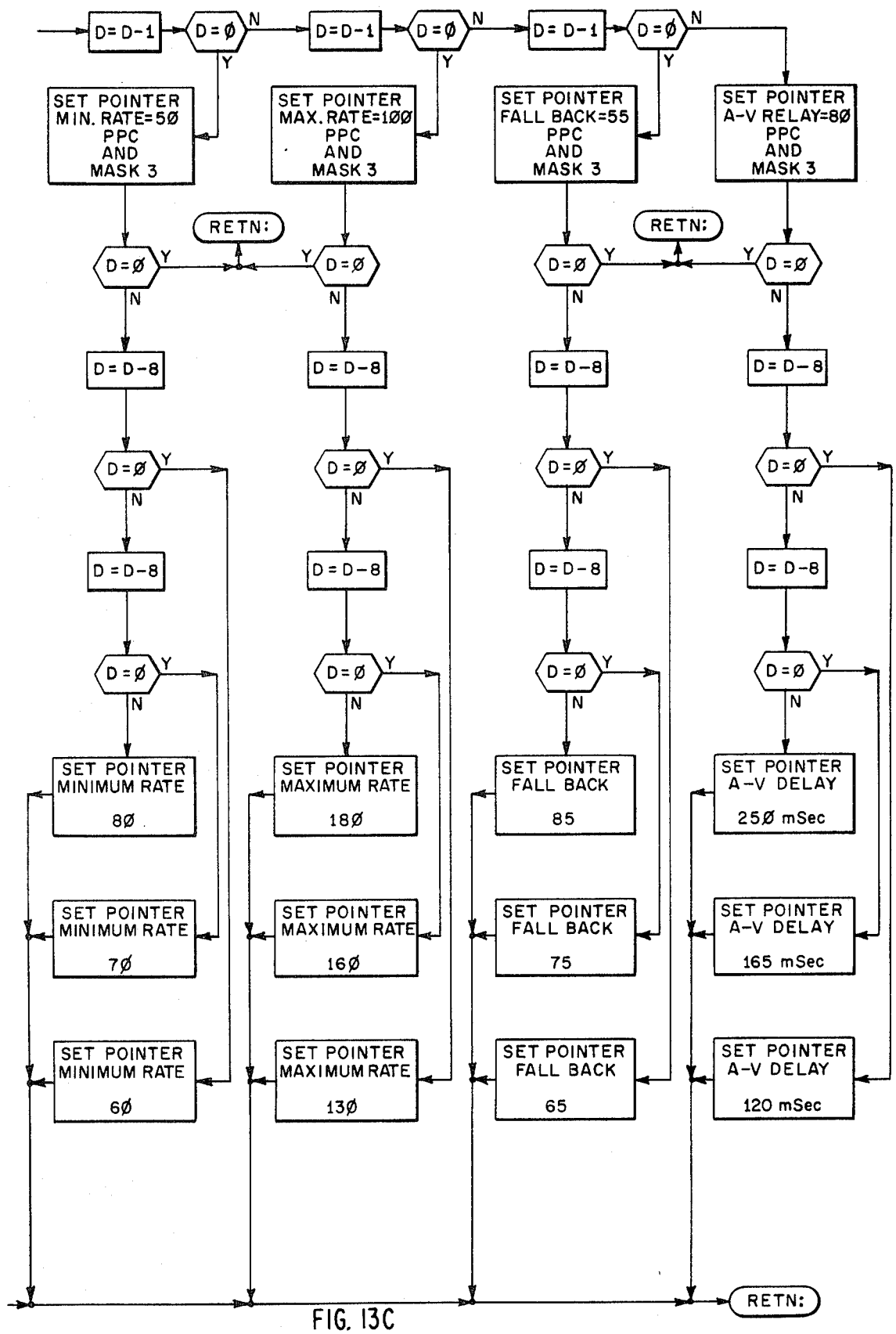

The flow chart for the programming routine is shown in FIGS. 13A, 13B and 13C. Programming is accomplished by any Cordis Corporation Model 222B programmer using the program card shown in FIG. 14 for reference. The program is encoded by turning a knob on the right of the programmer to one of the eight parameters as indicated on the front of the program card and selecting the value A, B, C, or D by turning the left knob. After these two settings are made, and the middle slide switch is down, the program button on the programmer is depressed. The programmer automatically emits a train of a predetermined number of magnetic impulses at 333 Hz. The number of pulses is counted in the pacer and decoded by software to determine the programmed parameter and value. Because of the software band pass in microcomputer system of FIG. 1, only programmers with the 333 Hz pulse strain are acceptable. Programmers using a 666 Hz pulse train will misprogram the pacer.

The programming routine, as shown in the flow chart of FIGS. 13A, 13B, and 13C, is set up as an interrupt service subroutine. Thus, the pacer will suspend executing instructions in any other routine while it is decoding programming pulses. The routine is called by the interrupt request (INT)-bar. The program begins by resetting the Q line if it has been set thus turning off whatever stimulation may be in process and incrementing the program pulse counter (PPC) register R7 which starts off at zero. Next the routine interrogates the reed switch port, EF3, up to 7 times to see whether the reed switch is still closed. If the reed switch is closed EF3 will be "1". If after seven interrogations (3.5 ms) the reed switch is still closed, the CPU concludes that a permanent magnet is being used and calls the magnet rate subroutine instead of proceeding with the programming routine. However, if the reed switch opens within seven interrogations, the CPU proceeds to see whether the switch stays open for up to seven additional interrogations. When the reed switch is open EF3 will be "0". If the reed switch closes within seven interrogations, the microcomputer increments the PPC and repeats the reed switch interrogation loop. On the other hand if the reed switch remains open for longer than seven interrogations (3.5 ms), the CPU is instructed to conclude that it has seen the last programming pulse. If it determines that there have been at least eight program pulses (PPC minus 8 is greater than or equal to zero), then it will proceed to decode parameters and values.

When decoding is finished, the CPU will load one of the six registers RA through RF with addresses for atrial and ventricular pulsewidth, AV delay, maximum and minimum rate intervals and fall back rate. The other two programmable variables, ventricular and atrial sensitivity, are entered by setting or resetting the addressable latches E, F and G, H, respectively. The atrial and ventricular stimulation output pulsewidth is entered by placing in register RA (atrial) and RB (ventricular) the addresses of the stimulation subroutine corresponding to the selected pulsewidth for each channel. The maximum and minimum rate intervals, fall back rates and AV delays are found in look up tables beginning in memory location CF. Registers RC, RD, RE, and RF are used as pointers to these look-up tables.

After the parameter value has been programmed, the CPU returns to the place in one of the operating routines where it was interrupted. To reprogram all eight parameter values to other than standard values, eight separate interrupt cycles are necessary. However, the programmer is capable of issuing two other types of commands, namely standard and overdrive. In the standard setting of the middle switch on the programmer, a series of pulses greater than or equal to 42 is transmitted and decoded, and the standard routine is called in which the program simply returns to the beginning location STINT (FIG. 13A) reinitializes all the registers with the standard parameters and begins VVI pacing. If the number of pulses is 40 or 41, atrial or ventricular overdrive, respectively, is selected.

Overdrive Routine

The two overdrive modes are selected by turning over the program card in FIG. 14 and setting the knobs to the appropriate values. The right hand knob selects the atrial ventricular channel and the middle switch pushed to the farthest up position selects overdrive. When atrial overdrive is selected, the programming routine includes an initialization step which adjusts the atrial sensitivity to a special high level and enables atrial stimulation. When ventricular overdrive is selected, the atrial sensitivity is similarly adjusted and the ventricular stimulation is enabled. The overdrive routine and flow chart are shown in FIGS. 15 and 16. The overdrive routine is equivalent to the function of the Cordis "Ectocor" pacer, with sensing of overdrive (chest wall stimulation) being accomplished by the atrial sense amplifier exclusively and the output pulse going to the chamber of choice. In this mode an external "pacer" provides timing pulses which are sensed on the atrial amplifier and result in immediate stimulation. Thus, the ventricular rate can be completely controlled externally and adjusted at will. The routine uses the programmed minimum rate (RD) as the slowest allowable rate and the programmed maximum rate (RC) as the fastest allowable rate. The programmed maximum rate is therefore the software rate limit and the refractory period as shown in FIG. 15. The overdrive routine is left by programming to standard values. The overdrive routine begins at memory address "103" in hex digits at program location "OVDRV".

Magnet Rate Routine

The magnet rate routine is called by placing a permanent magnet over the pacer which closes the reed switch thus calling the interrupt programming routine. Since the reed switch remains closed for more than seven interrogations, the programming routine is dropped in favor of the magnet rate routine. The object of the magnet rate routine with normal battery power is to provide fixed rate dual channel pulses to allow the physician to verify the action of the pacer. There is no alert period necessary since there is no inhibit function in the magnet rate, as shown in the timing diagram in FIG. 17. The magnet rate routine is flow-charted in FIG. 18. In order to accomplish AV sequential stimulation, RTC is set to zero and incremented once per scan. The length of a scan through the magnet rate routine is 58 machine cycles as it is in the main pacing routine. This is necessary to be able to use RTC to time the AV delay and the end of the minimum rate interval. When RTC is exactly equal to the AV delay pointed to by register RF, the ventricular pulse occurs. When the atrial alert period is over, (i.e. RTC=minimum rate interval) the CPU tests the EF4 port for battery condition. If the battery voltage comparator indicates that $V_{DD}$ is above 3.85 volts, the magnet routine proceeds to produce an atrial stimulation pulse and reset RTC. If the battery voltage comparator indicates that $V_{DD}$ is below 3.85 volts, the CPU is instructed to omit atrial stimulation and just reset RTC. Because of the action of the dual clock circuit 14 (FIG. 6), the crystal oscillator will also be replaced automatically by the RC oscillator at about 15% lower frequency. Thus, when the battery is low, the pacer will appear as a ventricular asynchronous device (VOO) pacing about 15% slower than the programmed minimum rate. If the battery is good but the crystal has failed, the pacer will operate in the asynchronous AV sequential mode (DDO) at a rate at least 5% slower than the minimum rate.

If the pacer has outputs on both channels and is pacing within one bpm of the minimum rate, then the battery voltage is above 3.85 volts and is considered nominal.

The magnet rate routine tests to see whether the magnet is present on each scan. If the magnet has been removed from proximity with the pacer, the CPU jumps back to the RETURN routine and resumes pacing activity.

Ventricular Inhibited Pacing Mode

Figure 19:
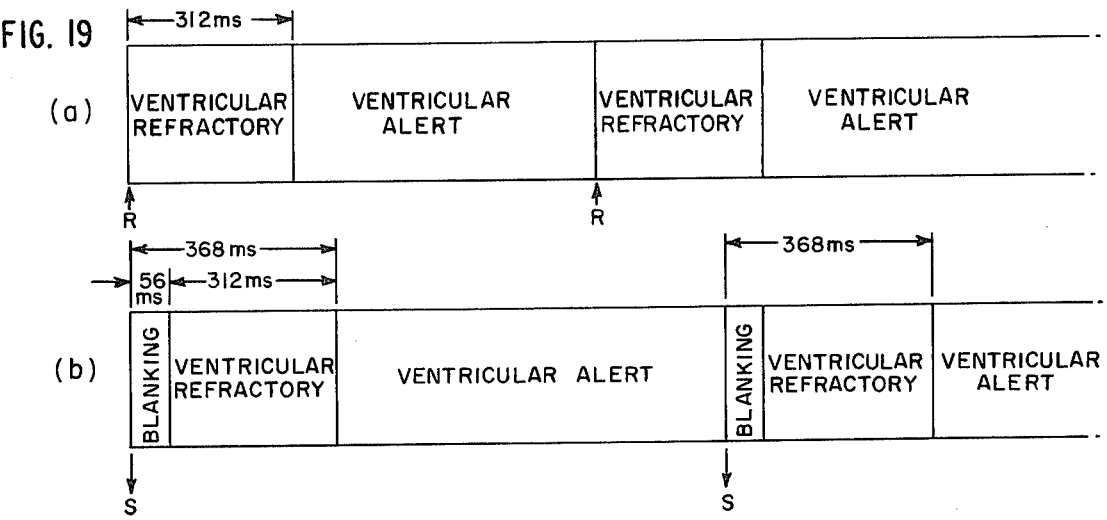
FIG. 19 is a timing diagram of the ventricular-inhibited pacing mode with the pacer of FIG. 1.

The pacer of FIGS. 1 and 2 is designed to be shipped in its ventricular-inhibited mode programmed to the standard set of parameter values. The atrial sensitivity and atrial output pulse duration are programmed in the initialization routine to "off". In the VVI mode, when the pacer senses ventricular activity occuring within the ventricular alert, the output is inhibited, as shown in line A of FIG. 19. If no ventricular activity occurs within the programmed minimum rate inverval, the ventricles are stimulated as shown in line B of FIG. 19.

In the VVI mode, AV delay, fall back rate and maximum rate are programmed, but they are for future use and they are not applicable in the VVI mode.

Atrial Synchronized Ventricular Inhibited Pacing Mode

Figure 20:
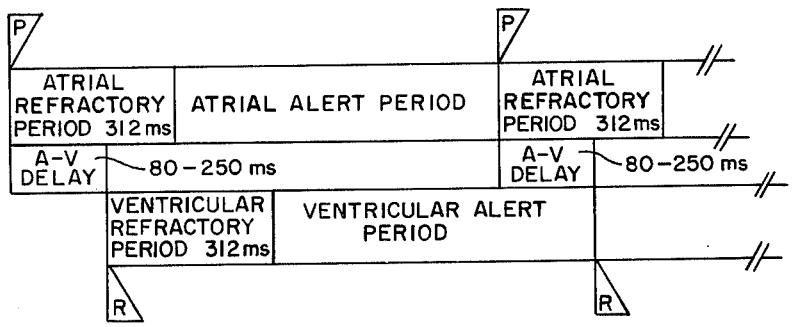
FIG. 20 is a timing diagram of the atrial synchronous ventricular-inhibited pacing mode with the pacer of FIG. 1.
Figure 21:
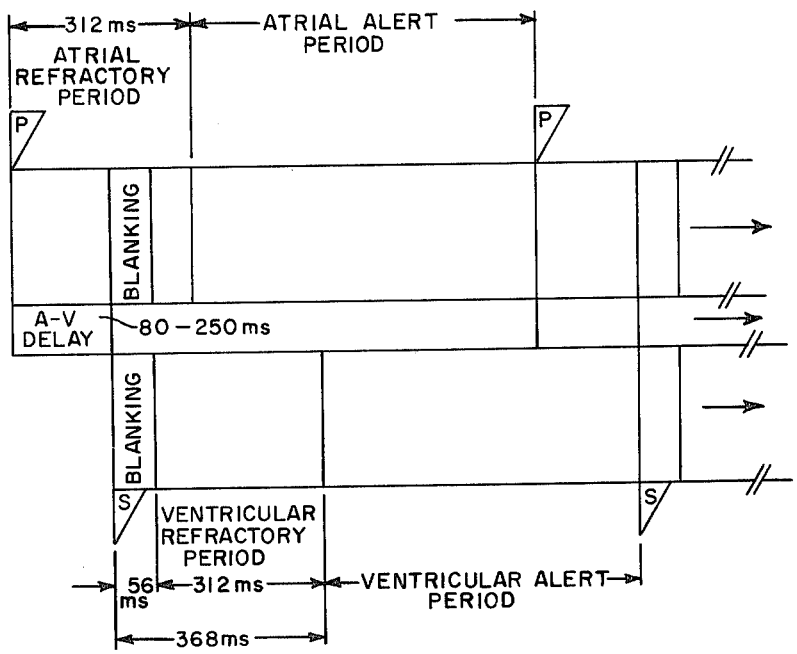
FIG. 21 is a timing diagram of the atrial synchronous ventricular-inhibited pacing mode of FIG. 20 in the absence of atrial activity.

To function in this mode, atrial output pulse duration should be programmed to off and the atrial and ventricular sensitivity programmed to 0.8 or 1.5 mV. As shown in FIG. 20 if normally the conduction occurs before the end of the programmed AV delay, the resulting ventricular activity is sensed and the ventricular activity is inhibited. If after sensing the atrial activity, no AV conduction occurs within the pacer's programmed AV delay, the ventricular channel paces the ventricles as shown in FIG. 21.

Figure 22:
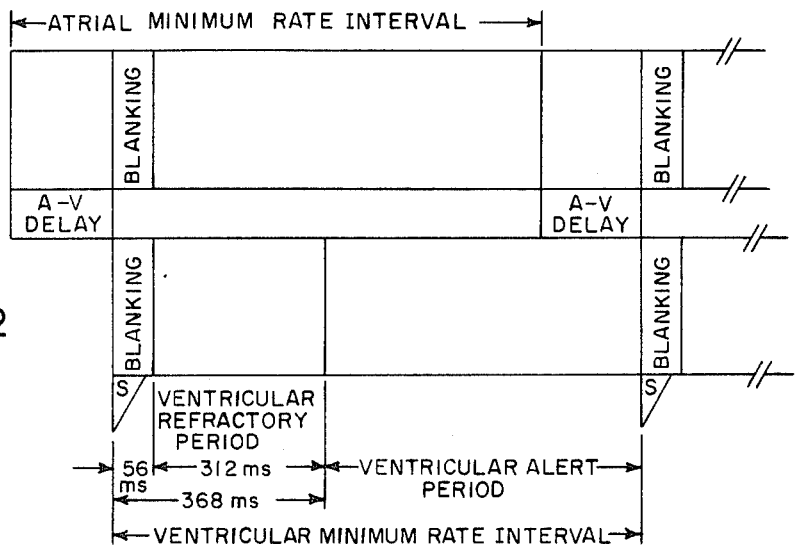
FIG. 22 is a timing diagram of the double demand pacing mode with both outputs inhibited in the presence of normal activity with the pacer of FIG. 1.

If no atrial activity is detected during the alert period of the atrial minimum rate interval, the ventricular channel paces the ventricles at the end of programmed AV delay. The ventricular channel functions as a fixed rate pacer stimulating the ventricle at the minimum programmed rate. Because the AV delay is fixed, the minimum rate interval is the same for the atrial and ventricular channels as shown in FIG. 22.

Atrial Synchronized Mode Without Ventricular Inhibition

To function exclusively in this mode, both the atrial output pulse duration and the ventricular sensitivity must be programmed to off. When so programmed the pacer senses atrial activity and paces at the end of the AV delay. The ventricular output will stimulate the ventricles in the absence of normally conducted ventricular activity or, when ventricular activity has resulted from AV conduction, the pacer's ventricular output pulse will fall in the absolute refractory period of the ventricles and is ineffective. This mode is not generally desirable for this reason. It can produce stimulation which competes with ectopic ventricular activity.

Atrial Inhibited, Atrial Synchronized, Ventricular Inhibited Mode

Programming the pacer from the standard values to suitable values for atrial sensitivity, atrial output pulse duration, maximum rate, fall back rate and AV delay permits the pacer to function either as atrial synchronized ventricular pacer or an AV sequential pacer. The pacer will automatically shift from one mode to the other depending on the patient's spontaneous atrial and ventricular rates, the condition of the AV conduction system and the programmed parameter values of the pacer.

Figure 23:
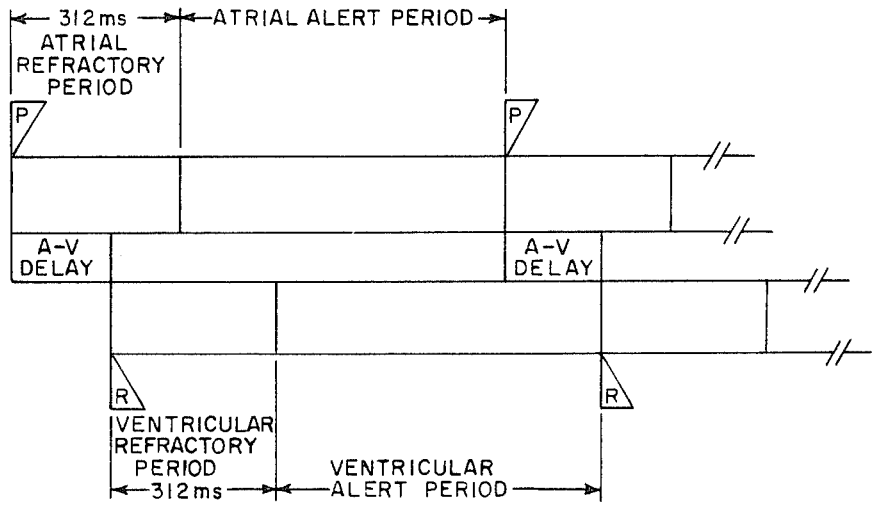
FIG. 23 is a timing diagram of the double demand pacing mode in the absence of AV conduction.

When the atrial rate is greater than the programmed minimum rate, the atrial output is inhibited. If AV conduction occurs resulting in ventricular activity before the end of the programmed AV delay, the ventricular output is inhibited. Full inhibition on both channels is illustrated in FIG. 23 by the appearance of P and R waves, respectively.

Figure 24:
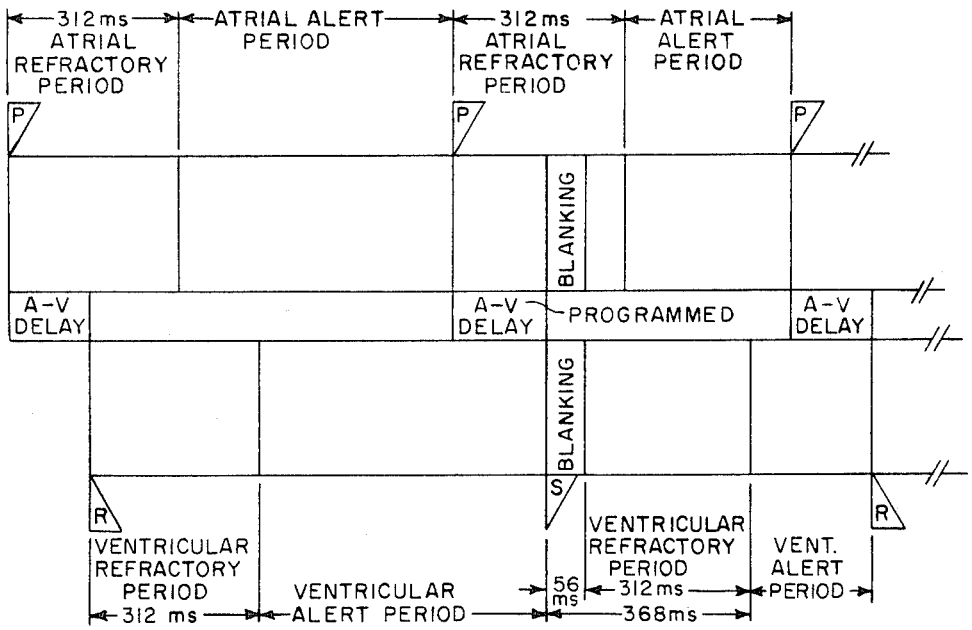
FIG. 24 is a timing diagram of the double demand pacing mode with variable AV conduction.

If no AV conduction occurs, or the conduction time is greater than the programmed AV delay, the ventricles are stimulated at the end of the AV delay period, as shown in FIG. 24 where the second P wave is followed by a fully expired programmed AV delay and a subsequent ventricular stimulation pulse. As the patient's AV conduction time changes the pacer will automatically shift from sensing ventricular activity and stimulate the ventricles when no ventricular activity occurs as shown in FIG. 24.

Figure 25:
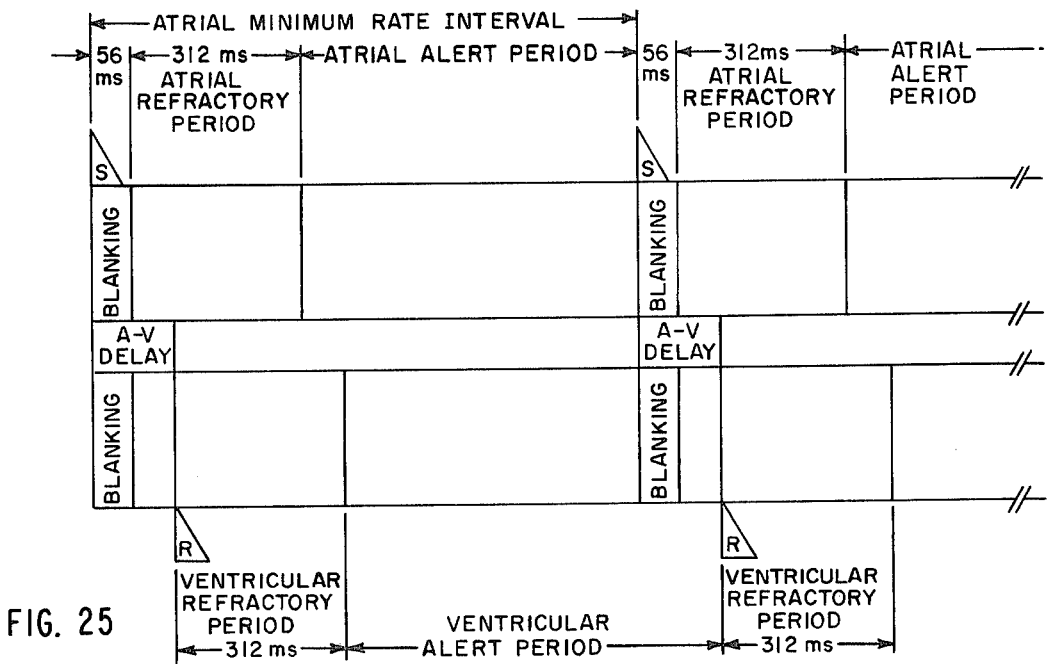
FIG. 25 is a timing diagram of the double demand pacing mode in the absence of atrial activity.

When the spontaneous atrial rate decreases below the programmed minimum rate, the pacer will stimulate the atria at the programmed minimum rate. In FIG. 25 the atria are being stimulated at the minimum rate and normal AV conduction occurs resulting in ventricular activity which inhibits the ventricular output.

When no spontaneous atrial activity is detected during the atrial alert period the pacer stimulates the atria. If by the end of the program AV delay no ventricular activity occurs, the pacer will also stimulate the ventricules as shown in FIG. 9 which illustrates double channel pacing.

Figure 26:
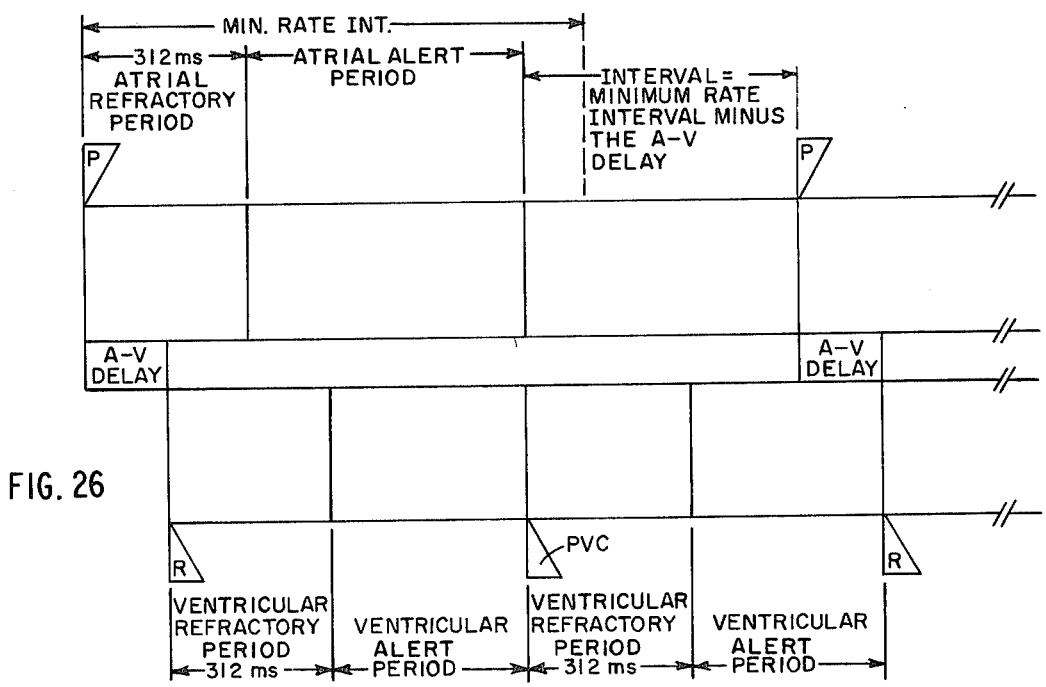
FIG. 26 is a timing diagram of the double demand pacing mode in response to a premature ventricular contraction.

The timing cycle of both channels is reset by ventricular activity if the pacer senses a premature ventricular contraction during the ventricular alert period. When this occurs, the real time clock is set to the AV delay period. Thus the interval after the sensed ventricular activity is the minimum rate interval minus the programmed AV delay period, as shown in FIG. 26.

Response to Atrial Tachyarrhythmia

In response to increasing atrial rates caused by an atrial tachycardia, atrial flutter or atrial fibrillation, the ventricular channel disassociates itself from the atrial activity. The ventricular channel automatically shifts to the VVI mode at a rate slightly less than programmed maximum rate. The ventricular rate will slowly decrease to the programmed fall back rate thereby protecting the ventricles from following the excessively high atrial rates while maintaining adequate hemodynamics. When normal AV conduction exists this change in mode in the presence of atrial tachyarrhythmia is not visualized on an electrocardiogram. Normally conducted ventricular activity inhibits the output of the ventricular channel during the decrease to the fall back rate.

To respond to an atrial tachyarrhythmia, the pacer must sense atrial activity occurring within the programmed maximum rate interval. When atrial sensitivity has been programmed to 0.8 or 1.5 Mv, atrial activity will be sensed and counted during the atrial refractory period, but the pacer cannot act on the information. The atrial arrhythmia count (R6) must have a count of 6 for the pacer to classify atrial tachycardia. At the maximum rate programmed, for example 180 bpm, and the fall back programmed to 85 bpm, slightly over 1 and ½ minutes are required to attain programmed fall back rate. The fall back rate can be easily identified on an ECG because these rates of 55 or 65, 75 and 85 are not available for programming as either the maximum or minimum rate. If the atrial rate has decreased sufficiently prior to returning to the fall back rate, the pacer will never attain the fall back rate but will simply return to the programmed mode at any time when no atrial activity occurs in the maximum rate interval for two consecutive cycles. In slowly reverting to the fall back rate, the pacer approximates the physiological decrease in normally conducted rate after stress.

Overdrive Pacing Mode

Reversing the programmer control card and inserting it into the programmer provides a reference for programming the pacer for overdrive. The chamber which is to respond to overdrive (chest wall stimulation) is selected. The other controls of the programmer must be in the overdrive positions as indicated by the card. The atrial overdrive parameter values are given below in Table 4.

| Parameters | Values |
|---|---|
| Atrial Sensitivity | 7 mV |
| Ventricular Sensitivity | Off |
| Atrial Output Pulse Duration | 2 ms |
| Ventricular Output Pulse Duration | Off |
| AV Delay | No meaning |
| Fall Back Rate | No meaning |

The ventricular overdrive parameter values are the same as the atrial except that the atrial output pulse duration is programmed to off and the ventricular pulse duration is 2.0 ms. The programming sequence for the overdrive mode does not change either the minimum or maximum programmed rate. These rates may be changed to higher or lower values as dictated by the patient's condition. The atrial or ventricular pacer output will follow the chest wall stimulation rate up to the pacer's programmed maximum rate or down to the minimum programmed rate. The pacer must be reprogrammed to the standard values after chest pulse stimulation; only then can the pacer be reprogrammed to the desired parameters.

The above described cardiac pacer meets the challenge of designing software and hardware as an integrated synergistic system to take advantage of the capabilities of microprocessing while conserving memory space and minimizing current drain. By design, a single main pacing routine serves for four different modes of operation which are selected by programming sense amplifiers and output pulses to the off condition as desired. The same programming routine not only monitors spontaneous activity of the heart in order to inhibit output pulses, but also monitors atrial pulses and decides whether they represent tachyarrhythmic activity. If they do, a special arrhythmia treatment routine is prescribed and applied. A failsafe clock system is included which automatically substitutes a reliable RC oscillator if the crystal fails. The low battery condition is doubly signalled by software and hardware changes, namely dropping the atrial beat and substituting the lower frequency oscillator. Among the numerous features and advantages of the invention are programmability by pre-existing magnetic programmers and automatic blanking of sense amplifiers.

Many variations and substitutions may be made in the above-described circuitry consistent with the fundamental principles of the invention. For example, the system may be modified for bipolar leads, or specified as an external pacer. While the programmability features are highly desirable, it is not essential to operation of the main pacing routine. For example, the pacer may be programmed by modifying the initialization routine in the software to operate in the atrial inhibited AV sequential ventricular inhibited mode. Software functions may also be executed by other types of microprocessors in an analogous fashion. For example, it is not necessary to use internal registers if additional random access memory space is provided. Moreover, although the digital circuits are designed for use in a single hybrid circuit, it may be feasible to incorporate most of the circuitry in a single custom VLSI chip.

Accordingly, as various changes can be made in the above construction without departing from the spirit or scope of the invention, it should be understood that all matter contained in the above description or shown in the accompanying drawings and appendices shall be interpreted as illustrative and not in a limiting sense.

What is claimed is:

1. A computer-controlled cardiac pacer, comprising
sense means for sensing cardiac activity and issuing a corresponding output signal,
computer means including digital storage means having stored program means containing a series of instructions and processing means for fetching and executing said instructions sequentially,
said stored program means including means defining recycling main pacing routine means,
said storage means including pacing parameter registers containing data indicative of a predetermined minimum rate interval and a scan register indicating the number of passes through said main pacing routine,
said main pacing routine means including
means defining a plurality of diverging and reconverging alternate instruction sequence loops each returning through a common instruction for incrementing said scan register, the time to execute a nominal loop being predetermined as a scan period,
loop adjustment means for making the time to execute each of the other loops equal to an integral number of scan periods, and
means for cyclicly monitoring the output of said sense means and the current number in said scan register during a given scan and said data in said parameter registers, for producing a programmed stimulation output when said scan register attains a number corresponding to said minimum rate interval and for resetting said scan register upon attaining a number corresponding to said minimum rate interval.

2. The pacer of claim 1, wherein said parameter registers include a first refractory register
said instructions including means for loading a predetermined number into said first refractory register,
said main pacing routine means including means for interrogating said first refractory register,
means for decrementing said first refractory register once per each pass through the main pacing routine, and
means for interrogating the output of said sense means only if said first refractory register has been decremented to a predetermined number indicative that the refractory period is over.

3. The pacer of claim 1, wherein said parameter registers include atrial and ventricular refractory registers,
said main pacing routine means including means for loading predetermined numbers into said refractory registers,
said main pacing routine means including means following said scan register incrementing instruction for defining ventricular activity module means followed by means defining an atrial activity module,
said ventricular module means including means for decrementing said ventricular refractory register if it is not zero proceeding to said atrial module,
means for interrogating the output of said sense means if said ventricular refractory register is zero,
means for reloading the ventricular refractory register if ventricular activity is indicated, means for resetting the scan register to a number equivalent to a programmed AV delay and returning to said scan register increment instruction, means for proceeding to the atrial module if ventricular activity is not indicated unless the scan register contains a number corresponding to a programmed AV delay, means for producing a programmed ventricular stimulation output while disabling said sense means if said scan register contains a number corresponding to the AV delay, means for loading the ventricular refractory register and returning to the scan register incrementing instruction, said atrial module means including means for decrementing said atrial refractory register if it is not zero and returning to the scan register incrementing instruction, means for interrogating the output of said sense means if said atrial refractory register is zero, means for reloading the atrial refractory register if there is atrial activity and resetting the scan register before returning to the scan register incrementing instruction, means for returning to the scan register incrementing instruction if there is no atrial activity unless the scan register contains a number corresponding to a programmed minimum rate interval, means for producing an atrial stimulation output while disabling said sense means if the scan register contains a number corresponding to a programmed minimum rate interval, means for reloading said atrial refractory register and means for resetting said scan register before returning to the scan register incrementing instruction.

4. The pacer of claim 3, wherein said stored program means includes means for selectively disabling said sense means and said stimulation output in order to realize a plurality of pacing modes.

5. The pacer of claim 1, wherein said stored program means further include means for causing said main pacing routine means to be selected, and further including means defining a plurality of other recycling pacing routine means each having a plurality of diverging and reconverging parallel alternate instruction sequence loops each returning through a common instruction for incrementing said scan register, the time to execute a nominal loop being predetermined as a scan period corresponding to that of the main pacing routine, loop adjustment means for making the time to complete each of the other loops equal to an integral number of scan periods, and other pacing routine means each including means for cyclically monitoring the current value in said scan register during a given scan, means for producing a programmed stimulation output when the scan register attains a predetermined number and means for resetting said scan register when it attains a number corresponding to a minimum rate interval, and
means for substituting one of the other pacing routines for said main pacing routine.

6. The pacer of claim 1, wherein the stored program means further includes means defining fallback pacing routine means,
said storage means further including a minimum rate interval register and a loop counter register,
means responsive to atrial tachycardia for substituting said fallback pacing routine means for said main pacing routine means,
said substituting means including means for initializing said loop counter register to a predetermined number corresponding to several seconds and means for loading a shortened minimum rate interval number into said minimum rate interval register,
said fallback routine means having a plurality of diverging and reconverging alternate instruction sequence loops each returning through a common instruction for incrementing said scan register, the time to execute a nominal loop being predetermined as a scan period equivalent to that of the main pacing routine, loop adjustment means for making the time to execute each of the other loops equal to an integral number of said scan periods,
said fallback pacing routine means including means for decrementing the loop counter register once per scan through the fallback routine, means for causing a stimulation output to be issued whenever the scan register attains the current minimum rate interval number, means for incrementing the minimum rate interval register whenever the loop counter reaches zero and reloading the loop counter with a predetermined number, and means for ceasing to increment the minimum rate interval register when the number in said minimum rate register attains a number corresponding to a predetermined fallback rate, and
means responsive to the absence of atrial tachycardia during execution of the fallback pacing routine means for returning control of the pacer to the main pacing routine means.

7. The pacer of claim 6, wherein said means in said fallback routine means for incrementing the minimum rate interval register includes means for incrementing the minimum rate interval register by a number corresponding to one scan period each time the loop counter reaches zero.

8. The pacer of claim 1, or 7 wherein the scan period is on the order of 15 ms.

* * * * *